(12) United States Patent
Neamati et al.

(10) Patent No.: US 8,445,677 B2
(45) Date of Patent: May 21, 2013

(54) SUBSTITUTED PYRIMIDYL GUANIDINE DERIVATIVES HAVING ANTICANCER ACTIVITY

(75) Inventors: Nouri Neamati, Fullerton, CA (US); Jinxia Deng, Portage, MI (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/604,365

(22) Filed: Oct. 22, 2009

(65) Prior Publication Data
US 2010/0160313 A1 Jun. 24, 2010

Related U.S. Application Data

(60) Provisional application No. 61/107,537, filed on Oct. 22, 2008.

(51) Int. Cl.
*C07D 239/02* (2006.01)

(52) U.S. Cl.
USPC .................................................. 544/330

(58) Field of Classification Search
USPC .................................................. 544/330
See application file for complete search history.

(56) References Cited

U.S. PATENT DOCUMENTS

2006/0100225 A1* 5/2006 Chen et al. .................... 514/269

OTHER PUBLICATIONS

Fedora Grande, et al., "*Synthesis and antitumor activities of a series of novel quinoxalinhydrazides*"; Bioorganic & Medicinal Chemistry, vol. 15; (2007); pp. 288-294.
Xueliang Fang, et al, "*A Web-Based 3D-Database Pharmacophore Searching Tool for Drug Discovery*"; J. Chem. Inf. Comput. Sci.; vol. 42; No. 2; 2002.
Omoshile O. Clement, et al., "*Three Dimensional Pharmacophore Modeling of Human CYP17 Inhibitors. Potential Agents for Prostate Cancer Therapy*"; Journal of Medicinal Chemistry; 2003; vol. 46; No. 12, pp. 2345-2351.
Osman Güner, et al., "*Pharmacophore Modeling and Three Dimensional Database Searching for Drug Design Using Catalyst: Recent Advances*"; Current Medicinal Chemistry; 2004; vol. 11; No. 22, pp. 2991-3005.
Jinxia Deng, et al., "*Dynamic Pharmacophore Model Optimization: Identification of Novel HIV-1 Integrase Inhibitors*"; Journal of Medicinal Chemistry; 2006; vol. 49; No. 5, pp. 1684-1692.
Jinxia Deng, et al., "*Design of Second Generation HIV-1 Integrase Inhibitors*"; Current Pharmaceutical Design; 2007; vol. 13; pp. 129-141.
Raveendra Dayam, et al., "*Discovery and Structure-Activity Relationship Studies of a Unique Class of HIV-1 Integrase Inhibitors*"; ChemMedChem; 2006; vol. 1; pp. 238-244.
Mutasem O. Taha, et al.; "*Discovery of new potent human protein tyrosine phosphatase inhibitors via pharmacophore and QSAR analysis followed by in silico screening*"; Journal of Molecular graphics and Modeling; vol. 25; (2007); pp. 870-884.

* cited by examiner

*Primary Examiner* — Douglas M Willis
(74) *Attorney, Agent, or Firm* — DLA Piper LLP (US)

(57) ABSTRACT

Disclosed are pyrimidyl guanidine derivatives having anticancer activity. The pyimidyl guanidine derivatives have the structure:

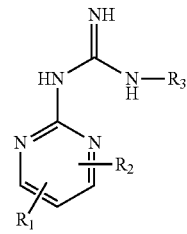

$R_1$ is a cyclic (1-7 member) or acyclic (1-7 member) aliphatic, aromatic, heterocyclic groups optionally substituted, $R_2$ is a cyclic (3-7 member) aliphatic, aromatic, heterocyclic groups optionally substituted by functional groups and $R_3$ is a cyclic (3-7 member) aliphatic, aromatic, heterocyclic groups.

1 Claim, 13 Drawing Sheets

SUBSTITUTED PYRIMIDYL GUANIDINE DERIVATIVES HAVING ANTICANCER ACTIVITY

The present application claims the benefit of the filing date of U.S. Provisional Application No. 61/107,537 filed Oct. 22, 2008, the disclosure of which is incorporated herein by reference in its entirety.

STATEMENT REGARDING FEDERALLY SPONSORED RESEARCH OR DEVELOPMENT

This invention was made with government support under Contract No. 0710414 awarded by the Department of Defense Ovarian Cancer Research Program. The government has certain rights in the invention.

FIELD OF THE INVENTION

The present invention relates in general to anti-cancer drug design. More specifically, the invention provides methods of mapping and screening for anti-cancer agents using Pharmacophore models.

BACKGROUND OF THE INVENTION

With the recent advances in targeted therapeutics and the progress in new approaches in target identification, novel anticancer agents with new mechanisms of action are under intensive investigation. Quinoxalinehydrazines represent a novel class of compounds with excellent potency in a panel of cancer cell lines.

Previously, we discovered a salicylhydrazide (SC) class of compounds with remarkable potency against several human cancer cell lines. SC141, a prototype of a series of quinoxalinhydrazides, showed in vivo efficacy in mice xenograft models of human breast cancer. We also reported structure-activity relationship studies by preparing a series of compounds using a one-step coupling of 7-fluoro-4-chloropyrrolo[1,2-a]quinoxalines with pyrazin-2-carbohydrazide.[1] The newly synthesized compounds were tested against four cancer cell lines using MTT and colony formation assays. The substitution at the 2-carbohydrazide moiety had a dramatic effect on the activity of the drugs. A representative compound, SC161, showed higher activity than other analogues.[1] We therefore explored SC161 as a lead molecule to design novel anticancer agents with greater potency and better pharmacokinetic properties.

Recently, we presented a 10 ns molecular dynamics (MD) simulation of SC161 followed by a seven feature pharmacophore model development according to the most probable conformation to capture the high probabilistic feature orientation. Its application to database mining successfully identified several potent agents, and some of the compounds showed comparable activity profiles with SC161.

The pharmacophore concept has been widely accepted as an efficient tool for use in combination with other technologies in drug design and optimization.[2-6] Pharmacophore is defined as a three-dimensional (3D) arrangement of chemical features (functional groups), which is responsible for the compound to be active against an enzyme or receptor. A pharmacophore derived on the basis of a bonafide lead compound can be used as a search query to retrieve compounds with diverse structural scaffolds from a database of compounds.[7] In general, pharmacophore models can be generated either using a set of known inhibitors of an enzyme or the active site of the enzyme. Analogue-based pharmacophore models are generated by utilizing a set of known inhibitors. The use of pharmacophore models as search queries are expected to retrieve novel compounds that contain desired pharmacophoric features with diverse structural and chemical features. These compounds are then expected to bind the drug target in a similar manner as the model compounds and to exert a similar biological response. This provides an extensive chemical space for lead identification and optimization. Structure-based pharmacophore models are generated based on key chemical features in the active site of an enzyme. The use of models as search queries is expected to retrieve compounds containing complementary pharmacophoric features and shape. When the structural information of the receptor is unknown, the analogue-based approach is effective to define a pharmacophore model. A receptor-based approach requires detailed and accurate information on the key features of the enzyme active site that are involved in drug binding.[7] Both pharmacophore model approaches have been successfully applied to identify novel inhibitors specific to certain drug targets.[8-10]

SUMMARY OF THE INVENTION

In one embodiment, the invention relates to compounds or compositions comprising anticancer agents.

For example, a compound of the invention may be of Formula 1, 2, 3, 4, or 5:

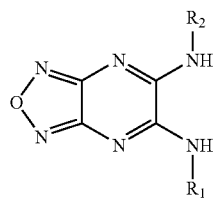

Formula 1

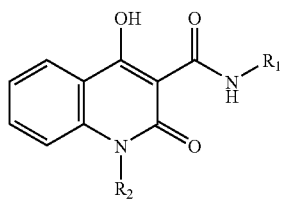

Formula 2

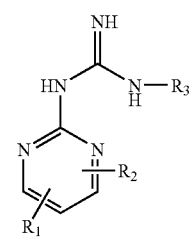

Formula 3

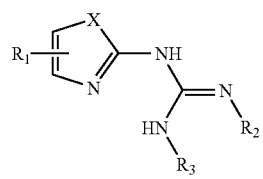

Formula 4

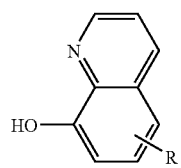

Formula 5

Representative compounds exemplified by Formula 1 are in Table 1 and the anticancer activities are given in Table 2.

R1 represents a variety of substitutions including but are not limited to hydrogen, halogen, hydroxyl, sulfhydryl, alkoxy, carboxyl, nitro, cyano, amino, amido, sulfonyl or any other organic functional group containing any number of carbon atoms.

R2 represents an aliphatic or aromatic group including alkyl, substituted alkyl, alkenyl, substituted alkenyl, alkynyl, substituted alkynyl, phenyl, substituted phenyl, aryl, substituted aryl, heteroaryl, substituted heteroaryl. Representative substitutions include but are not limited to halo, hydroxyl, sulfhydryl, alkoxy, carboxyl, carbonyl, nitro, cyano, amino, amido, sulfonyl and substituted heterocyclics.

Representative compounds exemplified by Formula 2 are in Table 1 and the anticancer activities are given in Table 2.

R1 represents an aliphatic, aromatic, heterocyclic groups including alkyl, substituted alkyl, alkenyl, substituted alkenyl, alkynyl, substituted alkynyl, phenyl, substituted phenyl, aryl, substituted aryl, heteroaryl, substituted heteroaryl. Representative substitutions include but are not limited to halo, hydroxyl, sulfhydryl, alkoxy, carboxyl, carbonyl, nitro, cyano, amino, amido, sulfonyl, sulfonamide and substituted heterocyclics.

R2 represents a variety of cyclic (3-7 member) aliphatic, aromatic, heterocyclic groups optionally substituted by functional groups including but are not limited to halogen, hydroxyl, sulfhydryl, alkoxy, carboxyl, carbonyl, nitro, cyano, amino, amido, sulfonyl, or sulfonamide.

Representative compounds exemplified by Formula 3 and the anticancer activities are given in Table 5.

R1 represents a variety of cyclic (1-7 member) or acyclic (1-7 member) aliphatic, aromatic, heterocyclic groups optionally substituted by functional groups including but are not limited to halogen, hydroxyl, sulfhydryl, alkoxy, carboxyl, carbonyl, nitro, cyano, amino, amido, sulfonyl, or sulfonamide.

R2 represents a variety of cyclic (3-7 member) aliphatic, aromatic, heterocyclic groups optionally substituted by functional groups including but are not limited to halogen, hydroxyl, sulfhydryl, alkoxy, carboxyl, carbonyl, nitro, cyano, amino, amido, sulfonyl, or sulfonamide.

R3 represents a variety of cyclic (3-7 member) aliphatic, aromatic, heterocyclic groups optionally substituted by functional groups including but are not limited to halogen, hydroxyl, sulfhydryl, alkoxy, carboxyl, carbonyl, nitro, cyano, amino, amido, sulfonyl, or sulfonamide.

Representative compounds exemplified by Formula 4 and the anticancer activities are given in Table 6.

R1 represents a variety of cyclic (1-7 member) or acyclic (1-7 member) aliphatic, aromatic, heterocyclic groups optionally substituted by functional groups including but are not limited to halogen, hydroxyl, sulfhydryl, alkoxy, carboxyl, carbonyl, nitro, cyano, amino, amido, sulfonyl, or sulfonamide.

R2 represents a hydrogen atom, cyclic or acyclic, straight or branched, saturated or unsaturated aliphatic, heteroaliphatic groups with optional substitutions, aryl or heteroaryl groups with optional substitutions. Representative substitutions include but are not limited to hydrogen, halogen, hydroxyl, sulfhydryl, alkoxy, carboxyl, carbonyl, nitro, cyano, amino, amido, sulfonyl, sulfonamide and substituted aromatics, or heterocyclics.

R3 represents a hydrogen atom, cyclic or acyclic, straight or branched, saturated or unsaturated aliphatic, heteroaliphatic groups with optional substitutions, aryl or heteroaryl groups with optional substitutions. Representative substitutions include but are not limited to hydrogen, halogen, hydroxyl, sulfhydryl, alkoxy, carboxyl, carbonyl, nitro, cyano, amino, amido, sulfonyl, sulfonamide and substituted aromatics, or heterocyclics.

Representative compounds exemplified by Formula 5 and the anticancer activities are given in Table 7.

R represents a variety of cyclic (1-7 member) or acyclic (1-7 member) aliphatic, aromatic, heterocyclic groups optionally substituted by functional groups including but are not limited to halogen, hydroxyl, sulfhydryl, alkoxy, carboxyl, carbonyl, nitro, cyano, amino, amido, sulfonyl, or sulfonamide.

In another embodiment, the invention relates to methods of generating pharmacophore models. The method comprises: (a) obtaining a lead compound conformation; (b) mapping the functional features of the lead compound; (c) performing a Molecular Dynamics (MD) simulation of the lead compound; (d) performing a cluster analysis of trajectories; and (e) selecting pharmacophore models exhibiting a representative conformation with cytotoxic properties or selecting pharmacophore models that were retrieved by multiple queries. The pharmacophore models preferably comprise oxadiazolopyrazine or quinolin motifs.

In a closely related embodiment, the invention relates to pharmacophore models. The pharmacophore models preferably comprise a oxadiazolopyrazine or quinolin motif.

In another embodiment, the invention relates to methods of screening anti-cancer agents using pharmacophore models. The method comprises: (a) obtaining a Pharmacophore model; (b) mapping the pharmacophore model against potential anti-cancer agents; and (c) selecting anti-cancer agents representing diverse chemical and structural space for cytotoxic properties.

In a related embodiment, the invention relates methods of identifying and testing anti-cancer agents. The method comprises: (a) obtaining a pharmacophore model; (b) mapping the pharmacophore model against potential anti-cancer agents; (c) performing cytotoxicity assays on anti-cancer agents representing diverse chemical and structural space for cytotoxic properties; and (d) identifying the anti-cancer agents with greater are equal cytotoxicity to the pharmacophore model.

A composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Compositions suitable for injectable use include sterile aqueous solutions (where water soluble) or dispersions and sterile powders for the extemporaneous preparation of sterile injectable solutions or dispersion. For intravenous administration, suitable carriers include physiological saline, sterile water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the compounds in the required amounts in an appropriate solvent with one or a combination of ingredients enumerated above, as required, followed by filtered sterilization. Generally, dispersions are prepared by incorporating the compounds into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the compounds can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compositions are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compositions of the invention can also be prepared in the form of suppositories (e.g., with conventional suppository bases such as cocoa butter and other glycerides) or retention enemas for rectal delivery.

In one embodiment, the compositions are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is advantageous to formulate oral or parenteral compositions in dosage unit form for ease of administration and uniformity of dosage. "Dosage unit form," as used herein, refers to physically discrete units suited as unitary dosages for the subject to be treated; each unit containing a predetermined quantity of active compound calculated to produce the desired therapeutic or effect in association with the required pharmaceutical carrier.

The compositions of the invention can be included in a container, pack, or dispenser together with instructions for administration to form packaged products. Other active compounds can also be incorporated into the compositions.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
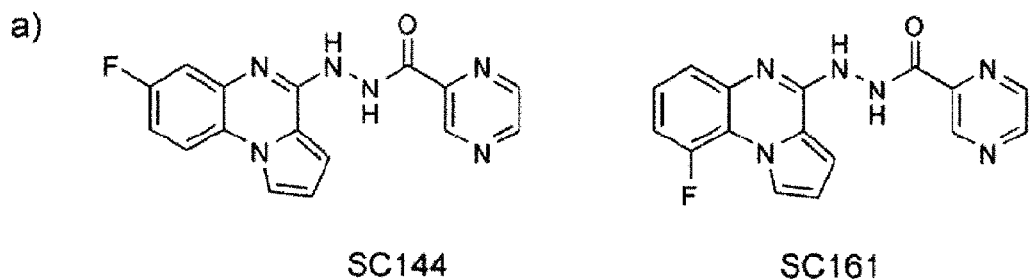
FIG. 1. Structures of (a) SC144 and SC161 and (b) parameters defined to monitor the conformational behavior of SC161. Defined variables: d1: O18-N24; d2: O18-N13; flexible torsion angles: t1: N13-C14-N15-N16, t2: C14-N15-N16-C17, t3: N16-C17-C19-C20; Planar angle is defined by two planes as represented by two gray surfaces: P1—C19N21N24 and P2—N5N13C14.
Figure 1:
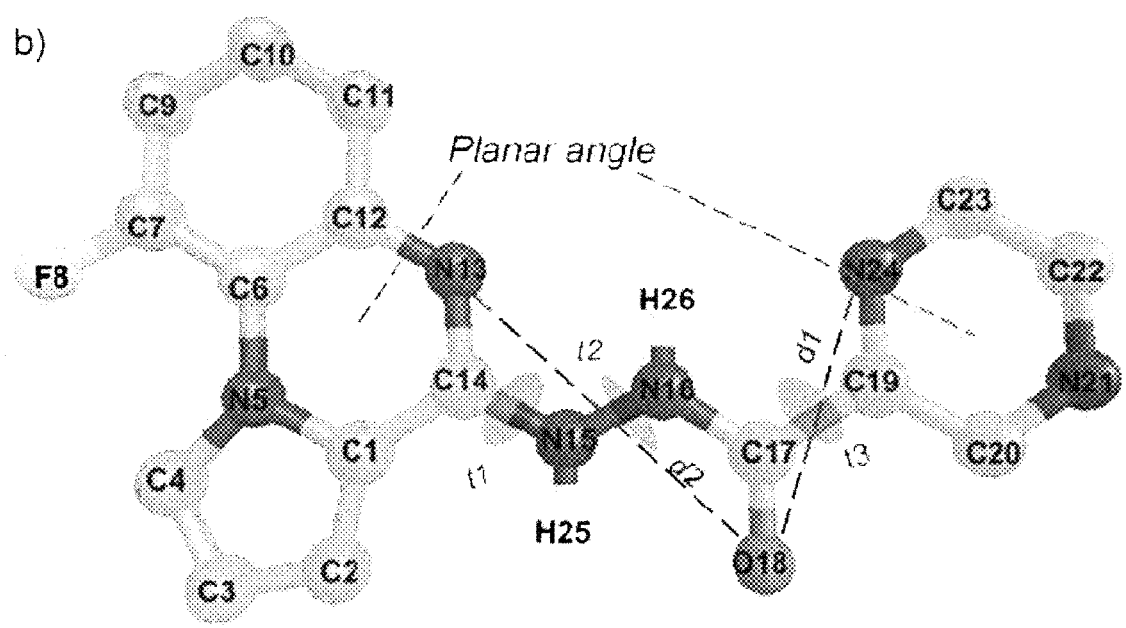

In a continuous effort to optimize the physicochemical properties of SC161, we generated a unique type of pharmacophore model, that we refer to as the Conformationally-Biased Common Feature model to generate possible feature combinations. The model development was based on dynamic behavior recorded form the same 10-ns MD simulations recently employed. Subsequently, the top-ten ranking pharmacophore models were applied to screen a subset of our small molecule database. Finally, we selected structurally diverse and novel compounds which were frequently retrieved by multiple-queries and tested them against a panel of cancer cell lines to validate their cytotoxicity.

Molecular Dynamics (MD)

MD studies of SC161 were carried out by GROMACS', a widely used software to simulate various biomolecular systems in aqueous or lipid bilayer environment.[15-19] The partial charges of SC161 with polar hydrogens were obtained by ab initio calculation using the unrestricted Hartree-Fock method in Gaussian program, at the High Performance Computer Center, University of Southern California. The basis set, the set of one-electron wave functions used to build molecular orbital wave functions, was set to STO-3G with spin multiplicity of 2. The topology file of SC161 consistent with GROMACS force field was generated by the PRODRG server, and was modified with the partial atomic charges by using the values calculated from the above ab initio procedure. Next, SC161 was centered in a box of 414 flexible SPC, or Simple Point Charge water molecules with a size of 2.82×2.49×1.86 $nm^3$. GROMACS force field was used to describe bonding and nonbonding interactions. The whole system was gradually equilibrated for 50 ps at 50K, 100K, 150K, 200K, 250K, and 300K. Finally, the production phase was simulated for 10 ns at 300K in a canonical ensemble (NVT, the number of particles N, the volume V and the temperature T were set to constant values). The chemical bond lengths involving hydrogen atoms were fixed using SHAKE algorithm.[7] A 2 fs timestep was used and both the energy and trajectory output were collected at 2 ps interval. Van der Waats interactions and short-range electrostatic interactions were truncated at 10.0 with the particle mesh Ewald method[21] setting used for long-range electrostatic interactions. Trajectory analysis including cluster analysis was carried out using the VEGA software package[22, 23] and recently reported elsewhere.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Example 1

Pharmacophore Model Development and Database Search

The Pharmacophore models were built on the selected snapshots of SC161 conformation, which were taken from the MD trajectory. Initially, Catalyst software (Accelrys, Inc.) package was used to import the SC161 conformation and map the functional features (H-bond donor, H-bond acceptor, hydrophobic feature, or aromatic ring) onto the frame. To develop the feature model, geometrical constraints were assigned to each feature. For example, coordinate and size of the feature, centered at the mapped atom or motif was assigned a radius of 1.3 Å for H-bond donor to avoid feature overlapping and 1.6 Å, for the rest of the features as default. Finally, all the selected features were merged into one pharmacophore model. The generated model was used as an independent search query to screen a subset of our 5,000,000 small-molecule databases. On the basis of intuitive structural classification, we selected compounds representing the diverse chemical and structural space for their cytotoxic properties. In this study, we focused on two classes of compounds representing oxadiazolopyrazines and quinolins.

Cytotoxicity Assay

Cell Culture.

Human breast cancer cells MDA-MB-435 were purchased from the American Type Culture Collection (Manassas, Va.). The HCT116 p53+/+ and HCT116 p53−/− cells were kindly provided by Dr. Bert Vogelstein (Johns Hopkins Medical Institutions, Baltimore, Md.). The human ovarian carcinoma cell line (HEY) which is naturally resistant to cisplatin, was kindly provided by Dr. Louis Dubeau, University of Southern California (USC) Norris Cancer Center, and NIH3T3 normal mouse fibroblast cells were kindly provided by Dr. Michael Press from USC. HEY and NIH3T3 cells were maintained as monolayer cultures in RPMI, HCT 116 cells in McCoy1s5A media and MDA-MB 435 in DMEM. Media were purchased from (Mediatech, Virginia) and supplemented with 10% fetal bovine serum (Gemini-Bioproducts, Woodland, Calif.), 2 mM L-glutamine and 5% Penicillin/streptomycin from Bio whittaker were purchased from VWR. Cells were incubated at 37° C. in a humidified atmosphere of 5% $CO_2$. To remove the adherent cells from the flask for passaging and counting, cells were washed with PBS without calcium or magnesium, incubated with a small volume of 0.25% trypsin-EDTA solution (Sigma-Aldrich, St. Louis, Mo.) for 5-10 min, and washed with culture medium and centrifuged. All experiments were performed using cells at exponential growth stage. Cells were routinely checked for mycoplasma contamination using a PCR-based assay (Stratagene, Tex., USA).

Drugs.

Stock solutions (10 mM) of all compounds were prepared in DMSO and stored at −20° C. Further dilutions were made fresh in PBS or cell-culture media right before cell treatment.

Cytotoxicity Assays.

Cytotoxicity was assessed by a 3-(4,s-dimethylthiazol-2-yl)-2,5-diphenyltetrazolium bromide (MTT) assay as previously described.[24] Briefly, cells were seeded in 96-well microtiter plates and allowed to attach overnight. Cells were subsequently treated with continuous exposure to the corresponding drug for 72 h. A MTT solution (at a final concentration of 0.5 mglml) was added to each well, and cells were incubated for 4 h at 37° C. After removal of the medium, DMSO was added and the absorbance was read at 570 nm. All assays were done in triplicate. The $IC_{50}$ was then determined for each drug from a plot of log (drug concentration) versus percentage of cells killed.

Colony Formation Assay.

Colony formation assays were also performed to confirm the activity of these compounds as described.[1,25] Briefly, cells were plated in 6-well plates at a density of 500 cells/well and allowed to attach. The next day, serial dilutions of the corresponding compounds were added and allowed to incubate for 24 h. After exposure, cells were washed in PBS and cultured in drug-free media until colonies were formed (8-10 days). Cells were subsequently washed, fixed with a 1% glutaraldehyde solution for 30 min, and stained with a solution of crystal violet (2%) for 30 min. After staining, cells were thoroughly washed with water. Colonies were imaged on the ChemiDoc Imaging System (Bio-Rad) and counted using the Quantity One quantitation software package (Bio-Rad). The data reported represent means of at least three independent experiments.

Results and Discussions

MD Trajectory and Cluster Analysis.

MD is a well-accepted molecular mechanics approach to sample the time dependent conformational change by solving Newton's equation of motion. Previously, we applied MD simulations to develop dynamic pharmacophore models bearing features complementary to HIV-1 integrase. The models were used as searching queries to screen small molecule databases and identified novel integrase inhibitor.[8, 26, 27] In this study, we collected data from SC161 simulation in its explicit water environment at the canonical ensemble. Energy profile over all the 10 ns showed that the whole system had an average potential energy of −16576.1 KJ/Mol with <0.59% fluctuation, and an average kinetic energy of 3189 KJ/Mol with <2.0% fluctuation. Therefore, the total energy of the whole equilibrated system was −13386 KJMol with 0.57% fluctuation, indicating the system was in its well established stable state. The average simulation temperature was at 300 K with fluctuation less than 6 K.

Defined Variables for Measuring the Conformational Change.

To monitor the conformational changes, six parameters were initially defined to analyze the dynamic behavior of SC161. As shown in FIG. 1, two variables, d1 and d2 were defined to sample the distance fluctuation between atom pairs N24 to 018, and 018 to N13, respectively. In addition, three flexible torsional angles were monitored during the simulations. Those were t1 defined by atoms N13-C14-N15-N16 t,2 defined by C14-N15-N16-Cla7n d t3 defined by atoms N16-C17-C19-C20. Last, a planar angle was defined describing the orientation between the planes set by the two aromatic fragments of SC161. Plane I (P1 hereafter) was defined by three atoms, C19, N21, and N24 of pyrazine motif, and plane II (P2 hereafter) was defined by N5, N13, and C14 of quinoxalin scaffold.

Correlations Among Defined Variables.

Figure 2A:
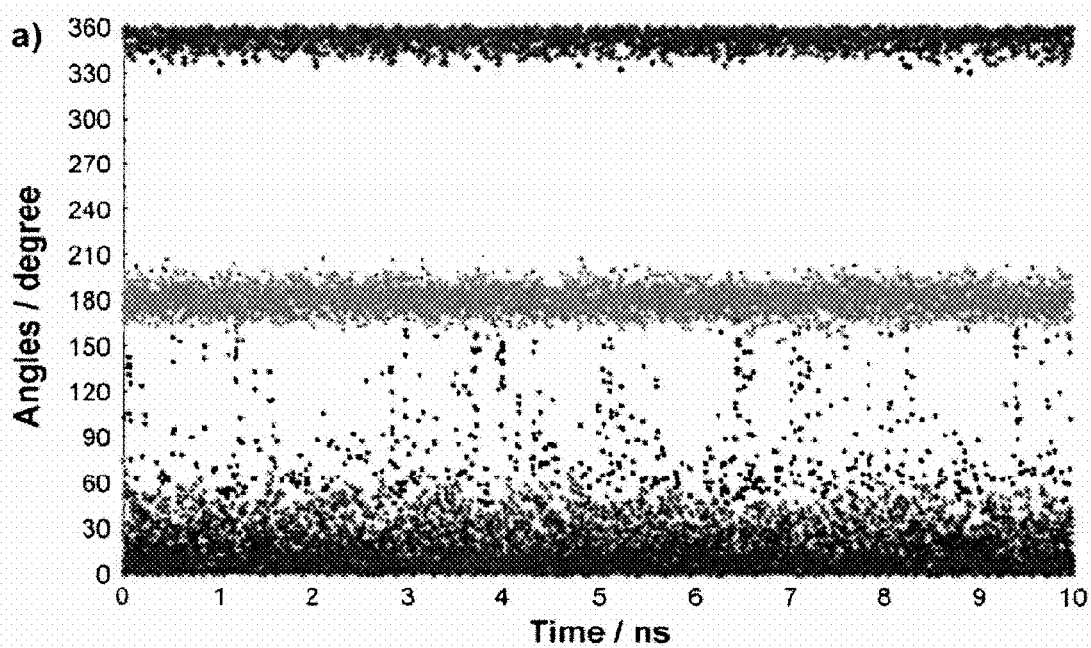
FIG. 2. Time dependence of the six defined variables. (A) Fluctuation of the three flexible torsional angles and the planar angle behavior during the simulation. t1: pink, t2: green, and t3: red. (B) Fluctuation of the two distance variables during the simulation, d1: pink and d2: blue.
Figure 2B:
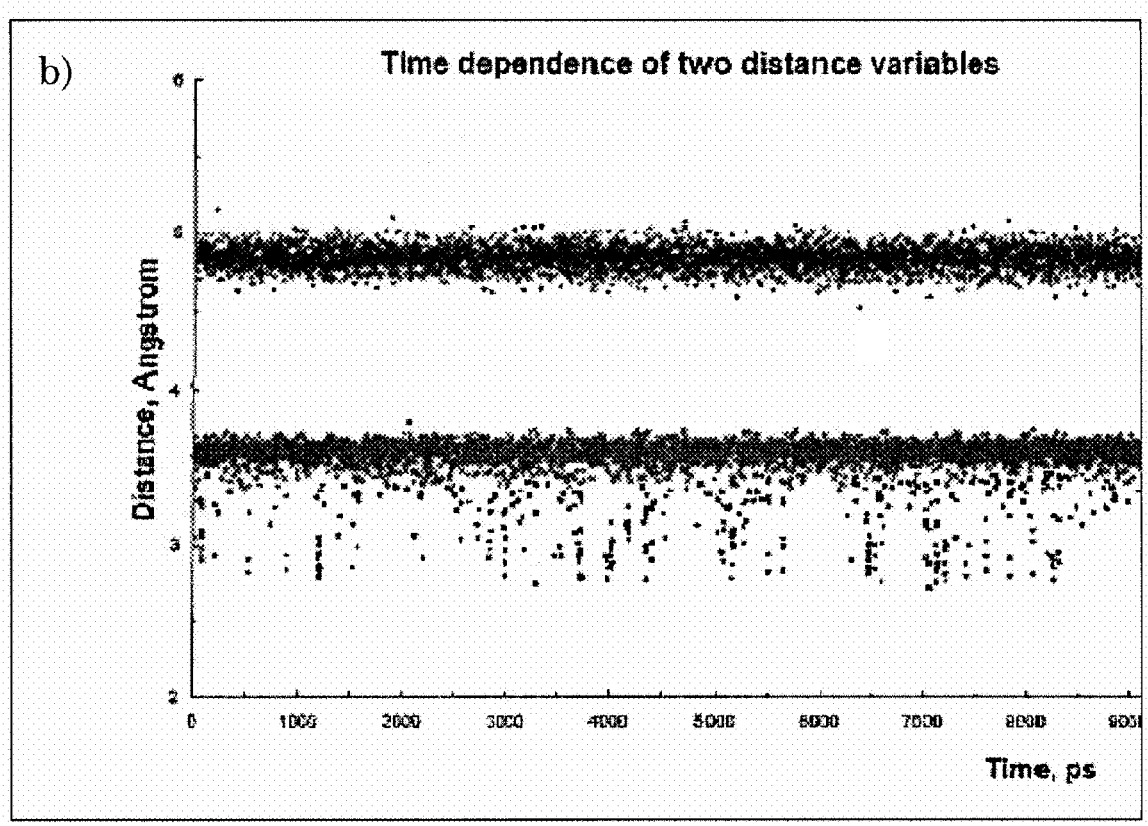

Apparently, the conformational behavior was strictly dependent on the three flexible dihedral angles, which could consistently be monitored by the above defined planar angle and the two distances d1 and d2. FIG. 2 describes the dynamic behavior of SC161 by means of the time-dependence of the defined variables. The snapshots were recorded at intervals of 2 ps, and the total of 5001 frames representing the 10-ns simulation studies. Among the three torsional angles (FIG. 2a), t1 is highly populated at a value close to 0° or 360° which represents the same orientation of the molecule, while t2 stabilizes at its average of 180.0° with very small fluctuation. This indicates that the two torsion angles, t1 and t2 are rather stable, and that no major conformational change occurred to the quinoxalinhydrazine motif of SC161 which is consistently depicted by the d2 index averaged at 4.8 Å±0.1 Å (FIG. 2b). This observation indicates that the conformational change is independent of t1, t2 and d2, which are therefore not considered for further conformational analysis. However, torsion angle, t3, apparently samples a higher angle space than t1 and t2 and its value covers an entire range of 0°-360°. This consequently leads to the wide range fluctuation of both planar angle value ranging from 0°-180°, and d1 value ranging from 2.7 A (cis position) to 3.8 Å (trans position) around its average of 3.5 Å. Therefore, the hydrazine motif actively flips at different angles leading to the various conformational clusters of SC161.

Figure 3:
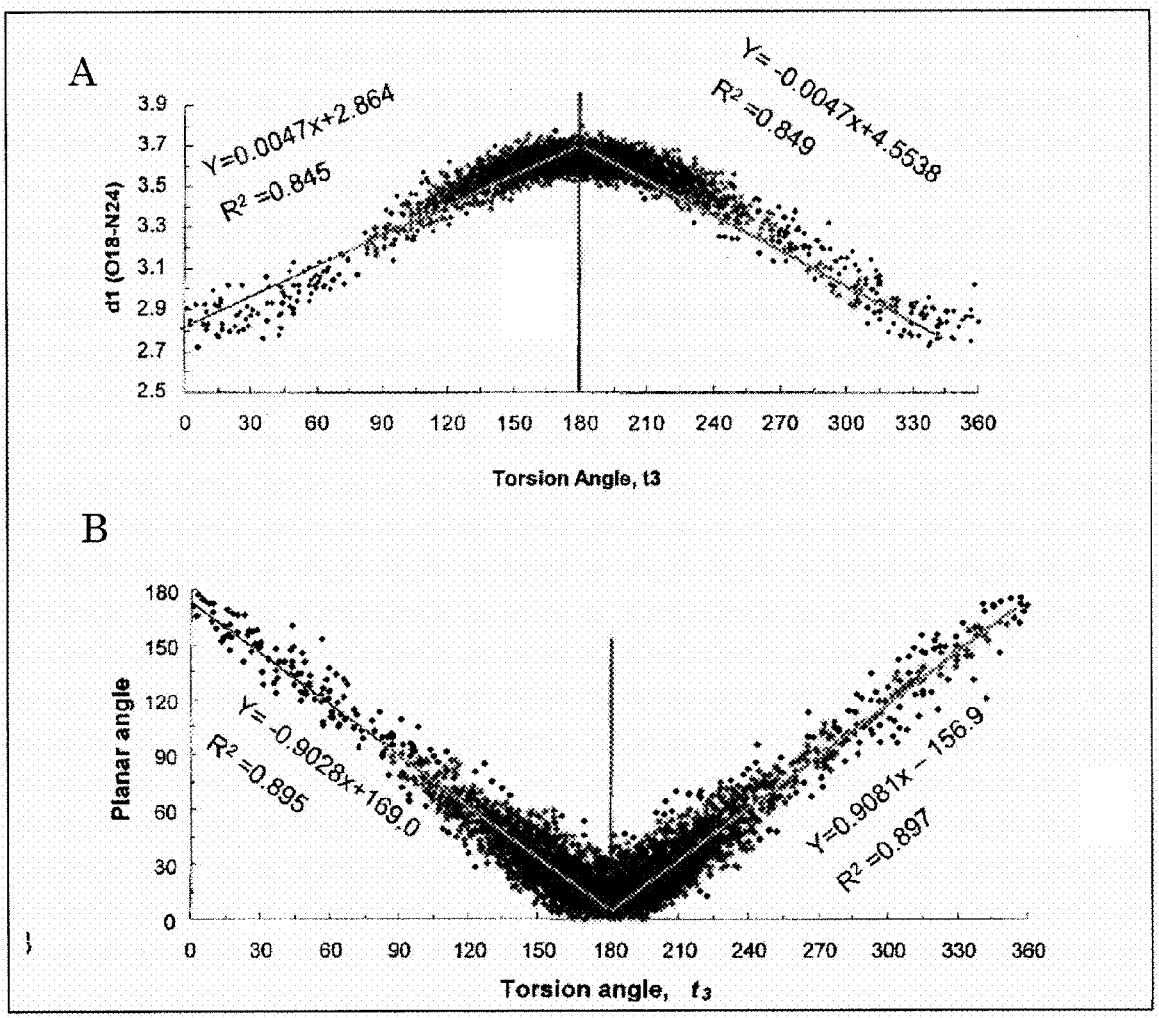
FIG. 3. Regression analysis shows linear relationship between distance d1 (O18-N24) and the torsion angle t3 (N13-C14-N15-N16), and strong correlation between planar angle and the torsion angle t3.

We performed further regression analysis for better understanding the correlation of torsion angle t3, distance d1, and planar angle. FIG. 3a shows a nearly symmetric profile of distance d1 versus torsion angle t3 with respect to the t3 value of 180°, and a strong correlation between d1 and t3 with the correlation coefficient of 0.92 ($R^2$=0.85). Likewise, the planar angle was selected and further correlated with the torsion angle, t3, as described by the scatter plot in FIG. 3b. This shows a strong linear correlation between the two variables as aligned well by the linear equation functions (symmetric with respect to the t3 value of 180) and with a correlation coefficient of 0.95 ($R^2$=0.895, 0.897, respectively). The regression analysis therefore suggests that the conformational change of SC161 solely depends on the behavior of torsion t3.

Snapshots Cluster Analysis.

Figure 4:
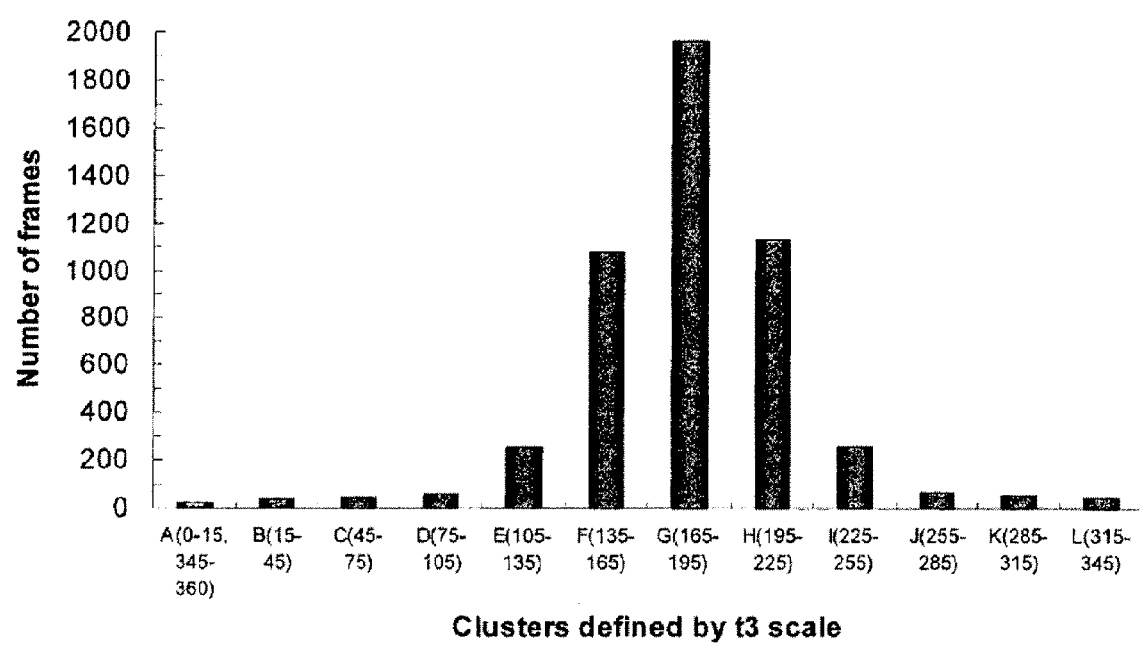
FIG. 4. Population of clusters grouped by the value range of torsion angle, t3. Each cluster covers the conformations with t3 values ranging within 30°. For example cluster B has frames with t3 ranging from 15-45° and cluster C with t3 values from 45-75°, and so on, except cluster A with t3 values in the range of 315-345°, and 0-15°.

As discussed above, we clustered the conformation of SC161 simply based on the distributions of t3 value, which were calculated from 5001 snapshots. FIG. 4 shows the population of the twelve clusters with an incremental step of 30° in t3 value. Due to the overlap between the conformations at t3 values of 0° and 360°, the first cluster (cluster A) contained the frames with t3 ranging from 0-15° and 345°-360°. Subsequently, cluster B was formed by frames with t3 values of 15-45°, C with t3 values of 45-75° and so on till the twelfth cluster L formed at last. The population of cluster frames shows a Gaussian distribution (FIG. 4) with the peak value of 1961 snapshots reached in the middle cluster (G) of t3 range between 180°±15°.

Pharmacophore Development, Database Screenings and Cytotoxicity Assays.

Figure 5:
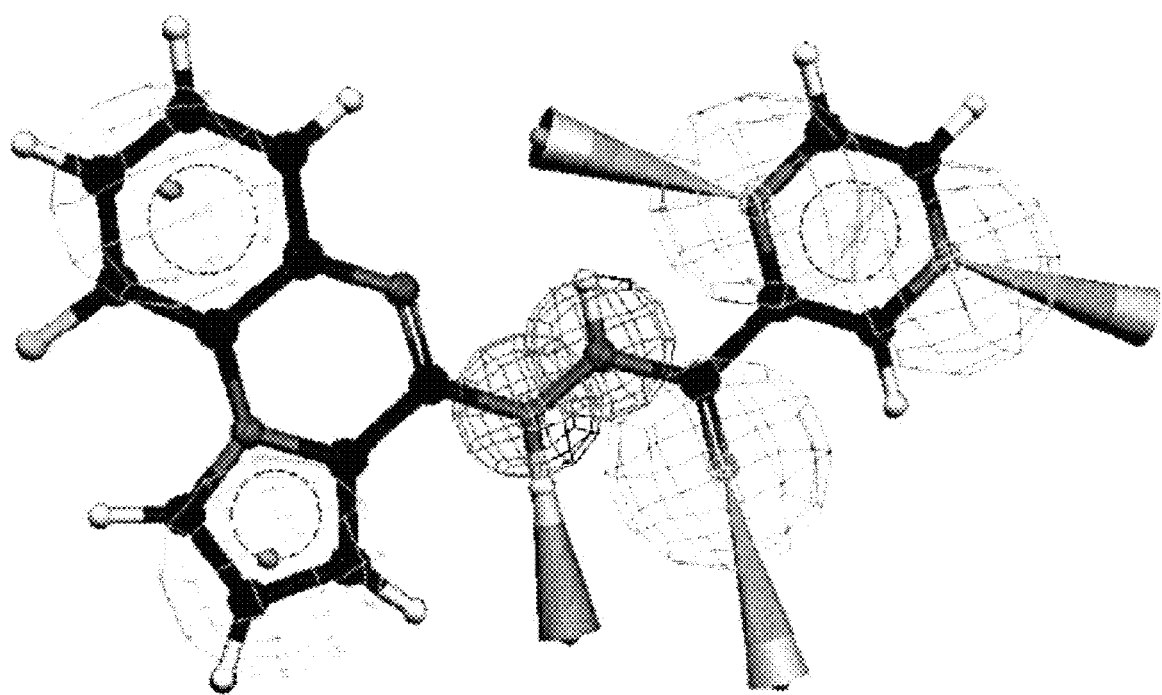
FIG. 5. The 7-feature model, based on the average structures of the SC161 top-sized cluster, mapping against SC161. Green represents H-bond acceptor; pink represents H-bond donor, and light blue represents hydrophobic feature.

On the basis of the above cluster analysis, we focused on the conformations collected in the top-ranked cluster G to build the pharmacophore model. The average structure of the snapshots was first generated, which essentially characterized the dynamic behavior of the frames in the cluster. Then, seven features were mapped onto the average structure. They are three H-bond acceptors defined by nitrogens of pyrazine and oxygen atom of the ketone, two H-bond donors defined by the hydrazine linker, and the two hydrophobic features were defined by the three-ring fragment of SC161 (FIG. 5).

The pharmacophore model was applied to a subset of our database containing 350,000 small molecules where each compound is represented by an ensemble of up to 250 conformations. All together, 938 compounds were mapped by the derived model. With considerations for structural diversity and calculated pharmacokinetic properties, we initially tested 20 compounds and realized that those with oxadiazolopyrazine or quinolin motif showed significant cytotoxicity. We thus extended our search to include more compounds bearing the same scaffolds. Therefore, a total of 35 novel compounds were tested for their cytotoxic properties in a panel of cancer cell lines.

Figure 6A:
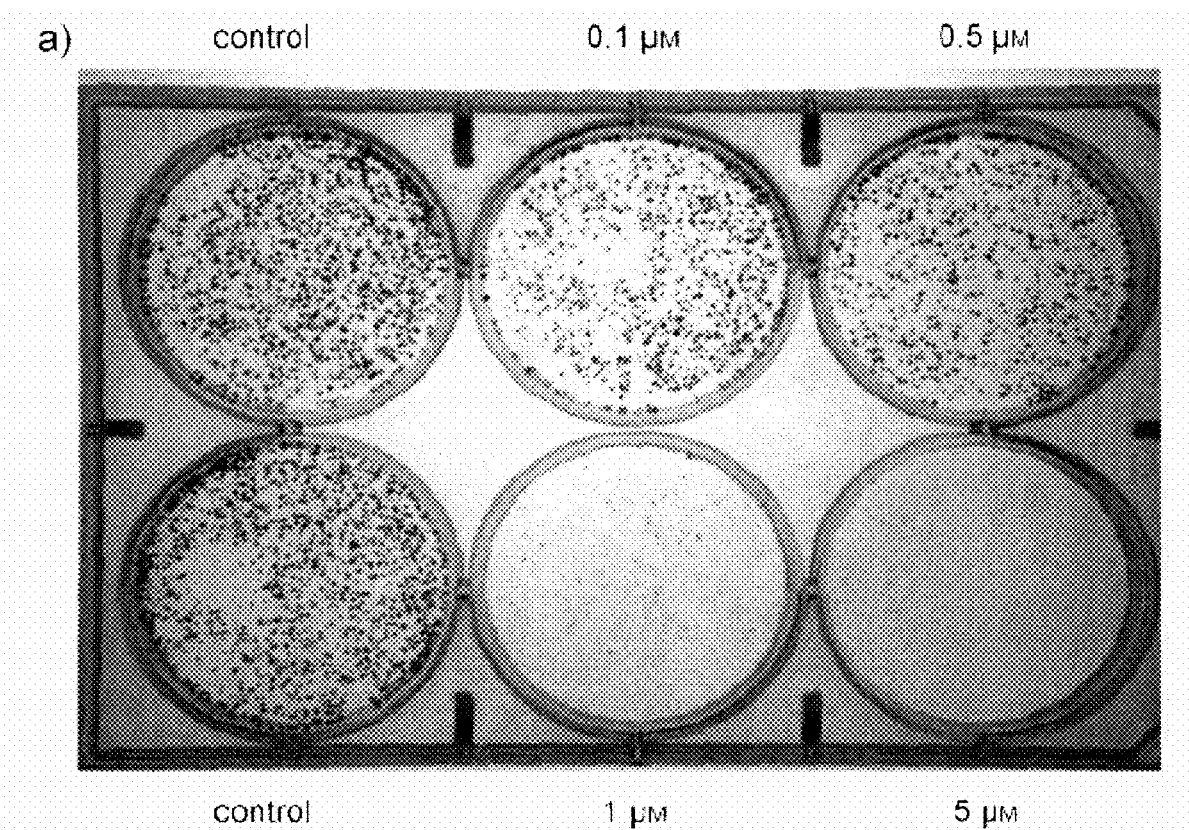
FIG. 6. Results of a colony formation assay in HCT p53+/+, and HEY cells treated with 2 at various doses. Compound 2 shows significant toxic effect in HCT p53+/+ (A) and HEY cells (B) as observed by colony formation assay of treatment on HCT p53+/+ and HEY cancer cells at several doses. At drug concentration≧1 μM, more than 95% of colonies were killed in HCT p53+/+ cells.
Figure 6B:
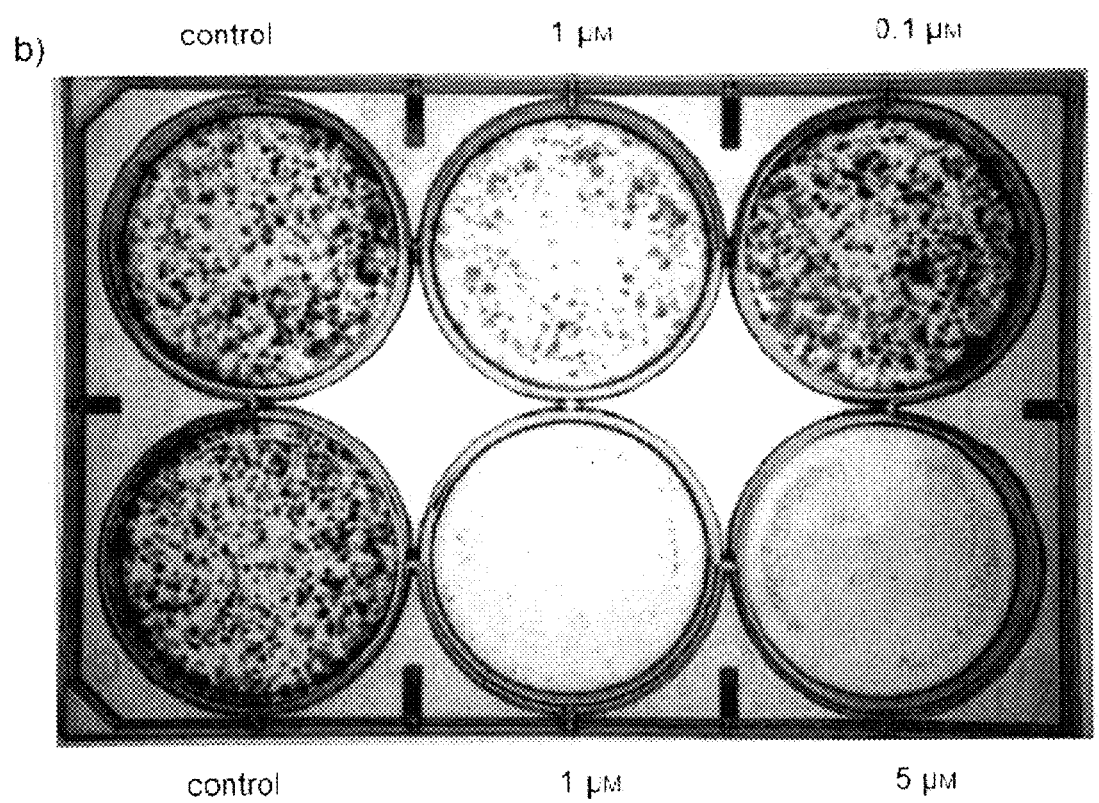

Table 1 lists the compounds identified from this work along with their predicted physiochemical properties and model fitting values. Cytotoxicity of these compounds against a panel of cancer cell lines are summarized in Table 2. Seventeen compounds showed $IC_{50}$ values<10 µM. Representatives of the oxadiazolopyrazine containing compounds are 15, 2, and 6 with ICSO values<3 µM in MDA-MB-435, HCT116 p53+/+, HCT116 p53-/-, and HEY cells. Quinolin analogues such as 30 and 32 were, in general, less potent than oxadiazolopyrazines. The best compound, 2, displayed $IC_{50}$ values<2 µM in HCT116 p53+/+, HCT116 p53-/-, and HEY cells. Additionally, 2 also exhibited mild toxicity against NIH3T3 ($IC_{50}$=8 µM) Compound 15 exhibited $IC_{50}$ value of 2.8 µM and 6.1 µM against MDA-MB-435 cell and HEY cell, respectively. 19 was toxic to HCT116 p53+/+ and p53-/- cells, while not toxic to other selected cells at dose up to 10.0 µM. Cytotoxicity of 2 was further confirmed by colony formation assay. FIG. 6 shows a representative result of a colony formation assay in HCT p53+/+, and HEY cells treated with 2 at various doses. At a dose of 1 µM of 2, >95% colonies were killed in HCT p53+/+ cells.

Figure 7:
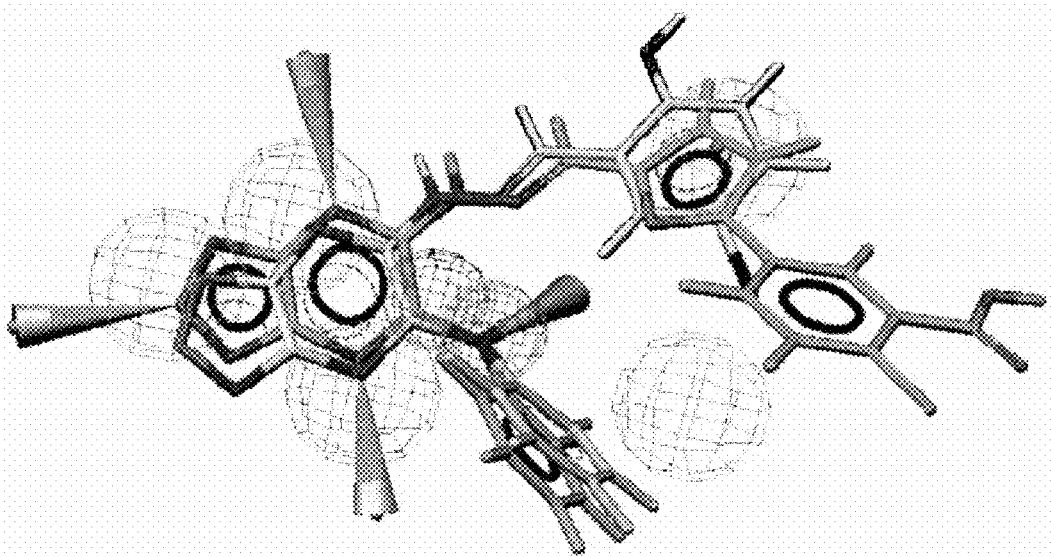
FIG. 7. Mapping of selected oxadiazolopyrazines, 2 and 17 against the pharmacophore model. Green represents H-bond acceptor; pink represents H-bond donor and light blue represents hydrophobic feature.

FIG. 7 shows the representative compounds, 2 and 17, mapped against the pharmacophore model derived from the structural conformations of cluster G. Because of the multiple conformations of each compound, various mapping orientations against the model were observed. In oxadiazolopyrazines, the three H-bond acceptors could favorably be mapped by the nitrogen atoms, while the N—H could map either of the H-bond donors. On the other hand, only one of the hydrophobic features could be mapped by the aromatic motif.

Example 2

Pharmacophore Model Development and Database Search

We applied the "HipHop" module in the Catalyst software package (Accelrys, Inc.) to generate a "qualitative model" based on multiple snapshot inputs without taking the biological data into consideration. This model represents the essential 3D arrangement of functional groups common to the selected set of molecules. In the traditional application of the module, the multiple molecules are the exact input set, however in this work, we concentrated on single active molecules but regarded the multiple conformations of the inputs as described below. We first created ten ensembles to represent the dynamic conformations of SC161. The 1001 frames of SC161 were collected at every 1ops interval of the 10-ns MD study, and were represented by 10 ensembles referred to as r1, r2 through r10. Each ensemble has 100 conformations or frames except rep1 which has 101 frames with 0-ps as the beginning snapshot. Therefore, r1 containing 101 conformations of SC161 covers the trajectory: 0 ps-1000 ps, 1-2: 1010 ps-2000 ps, r3: 2010 ps-3000 ps, r4: 3010 ps-4000 ps, and so on, through r10, which ranges from 9010 ps to 1011 s. The purpose of creating ten compounds representing the conformational diversity of SC161 is to generate a set of inputs for the common feature model development using the Catalyst software package. It is not necessary to use ten representations; we could divide the trajectory into any desired number of subsets as long as it is more than two, the minimum requirement of the common feature model approach.

Next, we mapped the compound with the chemical functions (H-bond donor, H-bond acceptor, hydrophobic, negative ionizable charge feature, and positive ionizable feature, etc) available from the feature dictionary in Catalyst. A total of ten top ranking hypotheses were collected and then used as 3D queries for database mining. On the basis of frequency of mapping by the various queries and the intuitive structural classification, we selected compounds representing diverse chemical and structural space for their cytotoxic properties. For this study, we initially tested 93 compounds in a panel of cancer cell lines.

Cytotoxicity Assay

Cell Culture.

Human breast cancer cell lines MDA-MB-435 and SkBr-3 were purchased from the American Type Culture Collection (Manassas, Va.). The HCT116 P53+/+ and HCT116 P53-/- cell lines were kindly provided by Dr. Bert Vogelstein (Johns Hopkins Medical Institutions, Baltimore, Md.). The HEY human ovarian carcinoma cell line was kindly provided by Dr. Louis Dubeau (University of Southern California Norris Cancer Center). Cells were maintained as monolayer cultures in media supplemented with 10% fetal bovine serum (Gemini-Bioproducts, Woodland, Calif.) and 2 mmo/lL-glutamine at 37° C. in a humidified atmosphere of 5% C02. To remove the adherent cells from the flask for passaging and counting, cells were washed with PBS without calcium or magnesium, incubated with a small volume of 0.25% trypsin-EDTA solution (Sigma-Aldrich, St. Louis, Mo.) for 5-10 min, and washed with culture medium and centrifuged. All experiments were performed using cells in exponential growth stage. Cells were routinely checked for mycoplasma contamination using a PCR-based assay (Stratagene, Cambridge, UK).

Drugs.

Stock solutions (10 mM) of all compounds were prepared in DMSO and stored at −20° C. Further dilutions were made fresh in cell-culture media just prior to cell treatment.

Cytotoxicity Assays.

Cytotoxicity was assessed by a 3-(4,5-dimethylthiazol-2-yl)-2,5-diphenyltetrazolium bromide (MTT) assay as previously described.[23] Cells were seeded in 96-well plates and allowed to attach overnight. Cells were subsequently treated with continuous exposure to the corresponding drug for 72 h. An MTT solution (at a final concentration of 0.5 mg/ml) was added to each well, and cells were incubated for 4 h at 37° C. After removal of the medium, DMSO was added and the absorbance was read at 570 nm. All assays were performed in triplicate. The $IC_{50}$ was determined for each drug from a plot of log (drug concentration) versus percentage of cells killed.

Results and Discussions

Figure 8:
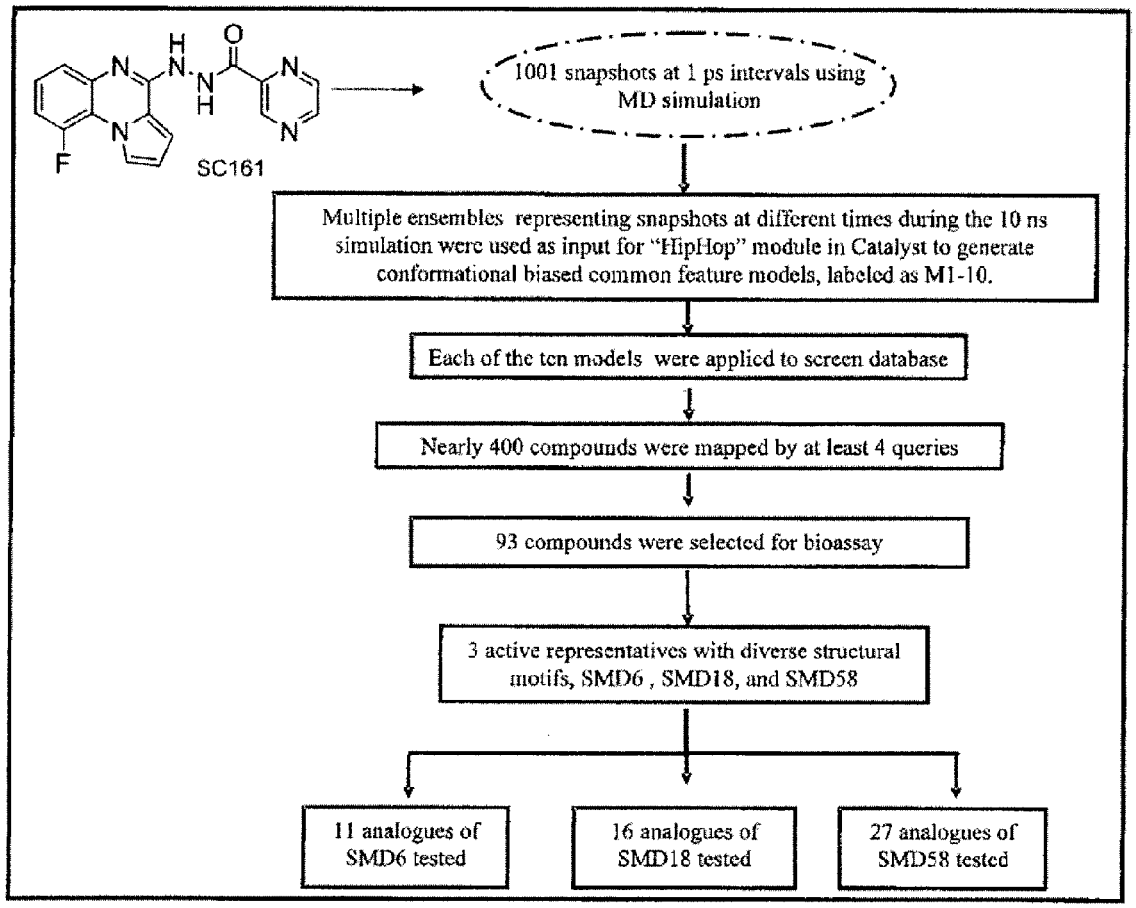
FIG. 8. The structure of SC161 and a flowchart outlining the steps taken to develop the pharmacophore model.

The overall strategies for deriving the novel Pharmacophore Model on the basis of SC161 and applying the pharmacophore models in retrieving novel compounds is summarized in FIG. 8.

Pharmacophore Development.

Figure 9:
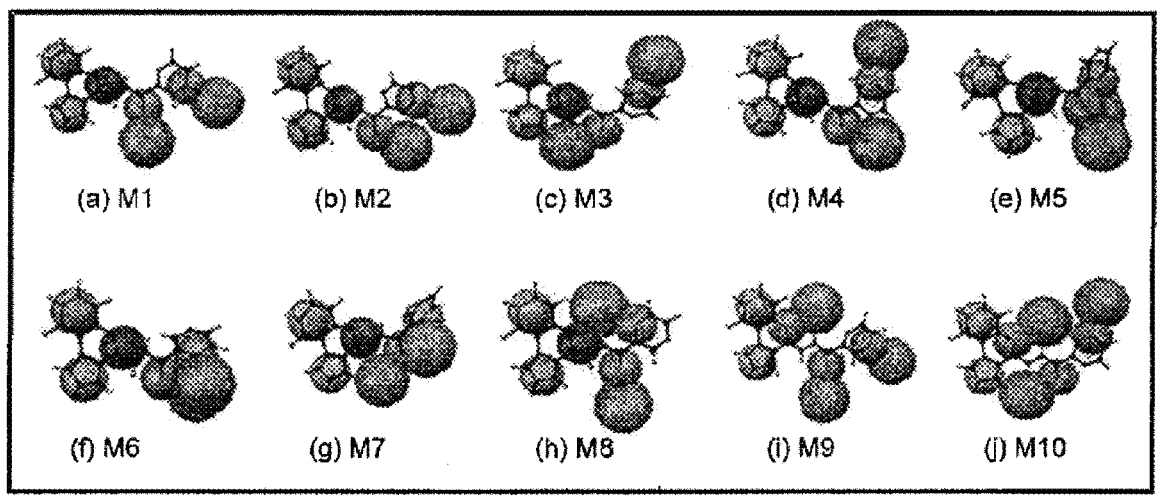
FIG. 9. SC161 mapping onto the top-ten ranking pharmacophore models generated by the Pharmacophore model approach as depicted in FIG. 8. Green represents H-bond acceptors. Red represents positive ionizable features and the light blue represents hydrophobic feature.
Figure 10:
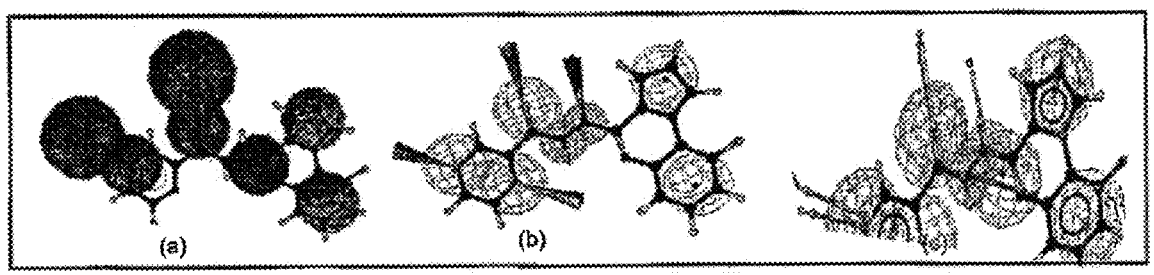
FIG. 10. (a) The top ranking common feature model MI overlaid by SC161. (b) The recently presented seven-feature model superimposed on SC161. (c) Two models overlaid on SC161. Green represents H-bond acceptors, and magenta represents H-bond donors. Red represents positive ionizable feature and SC161 is shown as a stick model.

The molecule SC161 is represented by a set of ten representative ensembles coving the entire trajectory of the 1001 frames taken from the 10 ns MD simulation. The top ten ranking common feature pharmacophore models, labeled as M1-M10 (FIG. 9) were generated on the basis of various conformational behaviors represented by the ten input ensembles. Each of the models has five features as listed in FIG. 9, which show the most favorable mapping of SC161 against each of the ten models. The features derived in the models are an H-bond acceptor, a hydrophobic feature or a positive ionizable feature. Table 3 summarizes the feature mapping of the exported hypotheses. According to the ranking score, these ten models have very close scores values. Each of the ten input ensembles could map all five-feature in the model as indicated by the value of "1" in the table about "direct hit mask", while the last part of "Partial Hit Mask" with value of "0" indicates that none of the molecules mapped all but one feature in the model. These hit masks provide a brief way together with the score as well to compare the common feature hypothesis. In Table 3, the pharmacophore models M1-M8 have similar types of features, i.e. two hydrophobic, one positive ionizable and two H-bond acceptor features. Models M9 and M10, however, have no positive ionizable features, but instead bear three H-bond acceptor features. The positive ionizable feature defined by Catalyst not only contains a single positively charged center, but it also includes those having the potential to be positively charged, such as primary, secondary or tertiary amide, amidine, and amidine with substituted hydrogen atom. In comparison with our recently published seven-feature model, which was derived from the single frame of the most probable conformation calculated from the same trajectory; four of the features from both models are conserved. These are the two H-bond acceptors mapped by the ketone oxygen or either nitrogen of the pyrazine, and the two hydrophobic features mapped by the pyrrolo-quinoxaline motif. Superimposition of the original seven-feature model and MI (the top-ranked model as a representative of the common feature models from this work), is shown in FIG. 10c while FIGS. 10a and 10b describe the individual mapping respectively. The two H-bond donors mapped by the hydrazine in the seven-feature model were not defined in this work. However, the positive ionizable feature was derived (M1-M8) based on the amidine scaffold of SC161, while an extra H-bond acceptor was defined by the quinoxaline nitrogen in M9 and M10.

Table 4 lists the cluster analysis of the ten models by hierarchical average linkage method available in Catalyst. If only two clusters formed, models M1-M8 are in the same cluster, while M9 and M10 are in the other cluster. Apparently, in most situations, the two models M9 and M10 are always clustered in the same group. Not surprisingly, in all circumstances, M1 and M2 are always in the same cluster because of the identical feature locations mapped against the same conformation of SC161; however, the orientation defined by both the small sphere and the big sphere pair of one H-bond acceptor mapped by a ketone motif is slightly different.

Database Screen and Cytotoxicity Assay.

In total, 93 compounds were selected from the database mapping against the pharmacophore models. Three compounds, SMD6, SMD18 and SMD58, displayed potency showing an $IC_{50}$<10 µM in SKBR-3, HCT116 p53+/+, and HEY cell lines. SMD58 was the most potent with an $IC_{50}$<3.5 µM in five cancer cell lines. We then carried out structure activity relationship (SAR) studies to test various analogues of SMD6, SMD18 and SMD58. The structures of these compounds, and their tested cytotoxic data are listed in Table 5-7. In addition, some inactive compounds are provided in the supporting information. Eleven substituents of SMD6 bearing N-(4,6-dimethylpyrimidin-2-yl)-acetamidin were tested. Three of these SMD6 analogues showed cytotoxicity at doses<10 uM. SMD6-4 and SMD6-8 had compatible toxicity profiles with an $IC_{50}$<3.0 uM in certain cancer cell lines. Furthermore, 16 additional SMD18 substituents were tested by MTT assay. Interestingly, only SMD18-7 and SMD18-14 showed slightly more potency than their parent SMD8, exhibiting activity at doses<10 uM Finally, we tested 27 additional compounds bearing the core of SMD58 (Table 6), and 16 of them showed potency against various cancer cell lines. Both SMD58 and SMD58-1 had an $IC_{50}$<1 uM in p53+/+ cell line indicating much more potency than SC161.

Figure 11:
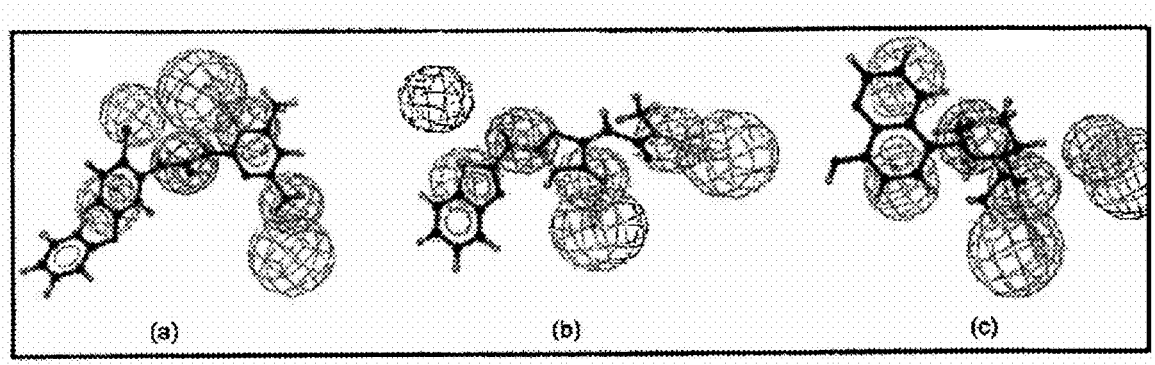
FIG. 11. Mapping the top three cytotoxic compounds against the common feature model. (a) SMD6 mapping against M3. (b) SMD18 mapping against MI. (c) SMD 58 mapping against M1 Green represents H-bond acceptors, and magenta represents H-bond donors. Red represents the positive ionizable feature and SC161 is shown as a stick model.

None of the ten models could map all three active compounds; however, SMD6 could be mapped by 4 models, M3, M7, M8, and M10. SMD18 could fit all ten models, while SMD58 could fit models M1-M8. The possible model mapping of the three potent compounds against certain pharmacophore model is depicted in FIG. 11.

Conclusions

Our 10 ns MD studies illustrate the dynamic behavior of SC161 and its preference for a planar conformation. As summarized in FIG. 8, the pharmacophore model using a unique approach derived from the ions-MD trajectory, was successfully applied to identify novel cytotoxic compounds. This method comprehensively takes into account all possible conformations of the small molecule. In this study, we show that conformational sampling of a single lead molecule is an efficient approach to build pharmacophore hypotheses and identify compounds with different physicochemical and drug like properties.

Many modifications and variation of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

1. Grande, F.; Aiello, F.; Grazia, 0. D.; Brizzi, A.; Garofalo, A; Neamati, N. Synthesis and antitumor activities of a series of novel quinoxalinhydrazides. *Bioorg Med Chem* 2007, 15, 288-294.
2. Milne, G. W.; Nicklaus, M. C.; Wang, S. Pharmacophores in drug design and discovery. *SAR QSAR Environ Res* 1998, 9, 23-38.
3. Fang, X.; Wang, S. A web-based 3D-database pharmacophore searching tool for drug discovery. *J Chem Inf Comput Sci* 2002, 42, 192-198.
4. Clement; O.; Freeman, C. M.; Hartmann, R. W.; Handratta, V. D.; Vasaitis, T. S.; Brodie, A. M.; Niar, V. C. Three dimensional pharmacophore modeling of human CYP17 inhibitors. potential agents for prostate cancer therapy *J Med Chem*, 2003, 46, 2345-2351.
5. Guner, 0.; Clement, 0.; Kurogi, Y. Pharmacophore modeling and three dimensional database searching for drug design using catalyst: recent advances. *Curr Med Chem* 2004, 11, 2991-3005.
6. Langer, T.; Hoffmann, R. D. Pharmacophores and pharmacophores searches (Methods and Principles in Medicinal Chemistry); Folkers, G. Ed.; Wiley-VCH, 2006.
7. Deng, J.; Dayam, R.; Al-Mawsawi, L. Q.; Neamati, N. Design of second generation HIV-1 integrase inhibitors. *Curr Pharm Des* 2007, 13, 129-141.

8. Deng, J.; Sanchez, T.; Neamati, N.; Briggs, J. M. Dynamic pharmacophore model optimization: identification of novel HIV-1 integrase inhibitors. *J Med Chem* 2006, 49, 1684-1692.
9. Dayam, R.; Sanchez, T.; Neamati, N. Discovery and structure-activity relationship studies of a unique class of HIV-1 integrase inhibitors. *Chem Med Chem* 2006, 1, 238-244.
10. Taha, M. O.; Bustanji, Y.; Al-Bakri, A. G.; Yousef, A. M.; Zalloum, W. A.; Al-Masri, I. M.; Atallah, N. Discovery of new potent human protein tyrosine phosphatase inhibitors via pharmacophore and QSAR analysis followed by in silico screening. *J Mol Graph Model* 2007, 25, 870-884.
11. Van Der Spoel, D.; Lindahl, E.; Hess, B.; Groenhof, G.; Mark, A. E.; Berendsen, H. J. GROMACS: fast, flexible, and free. *J Comput Chem* 2005, 26, 1701-1718.
12. Fu, W.; Shen, J.; Luo, X.; Zhu, W.; Cheng, J.; Yu, K.; Briggs, J. M.; Jin, G.; Chen, K.; Jiang, H. Dopamine D1 receptor agonist and D2 receptor antagonist effects of the natural product (-)-stepholidine (SPD): molecular modeling and dynamics simulations. *Biophys J* 2007.
13. Fan, H.; Mark, A. E.; Zhu, J.; Honig, B. Comparative study of generalized Born models: protein dynamics. *Proc Natl Acad Sci USA* 2005, 102, 6760-6764.
14. Gurtovenko, A. A; Vattulainen, I. Ion leakage through transient water pores in protein free lipid membranes driven by transmembrane ionic charge imbalance. *Biophys J* 2007, 92, 1878-1890.
15. James, J. J.; Lakshmi, B. S.; Raviprasad, V.; Ananth, M. J.; Kangueane, P.; Gautam, P. Insights from molecular dynamics simulations into pH-dependent enantioselective hydrolysis of ibuprofen esters by *Candida rugosa* lipase. *Protein Eng* 2003, 16, 1017-1024.
16. Palleschi, A.; Bocchinfuso, G.; Coviello, T.; Alhaique, F. Molecular dynamics investigations of the polysaccharide scleroglucan: first study on the triple helix structure. *Carbohydr Res* 2005, 340, 2154-2162.
17. Rockey, W. M.; Elcock, A. H. Rapid computational identification of the targets of protein kinase inhibitors. *J Med Chem* 2005, 48, 4138-4152.
18. Stahl, G. R.; Holtje, H. D. Development of models for cytochrome P450 2A5 as well as two of its mutants. *Pharmazie* 2005, 60, 247-253.
19. Verli, H.; Guimaraes, J. A. Molecular dynamics simulation of a decasaccharide fragment of heparin in aqueous solution. *Carbohydr Res* 2004, 339, 281-290.
20. Ryckaert, J. P.; Ciccotti, G.; ~erkndsenH., J. C. Numerical integration of the Cartesian equations of motion of a system with constraints; molecular dynamics of n-alkanes. *J. Comp. Phys.* 1977, 327-341.
21. Essmann, U.; Perera, L.; Berkowitz, M. L.; Darden, T.; Lee, H.; Pedersen, L. G. A smooth particle mesh Ewald method. *J. Chem. Phys.* 1995, 103, 8577-8593.
22. Pedretti, A.; Villa, L.; Vistoli, G. VEGA: a versatile program to convert, handle and visualize molecular structure on Windows-based PCs. *J Mol Graph Model* 2002, 21, 47-49.
23. Pedretti, A; Villa, L.; Vistoli, G. VEGA—an open platform to develop chemo-bioinformatics applications, using plug-in architecture and script programming. *J Comput Aided Mol Des* 2004, 18, 167-173.
24. Carmichael, J.; DeGraff, W. G.; Gazdar, A. F.; Minna, J. D.; Mitchell, J. B. Evaluation of a tetrazolium-based semi-automated colorimetric assay: assessment of chemosensitivity testing. *Cancer Res* 1987, 47, 936-942.
25. Munshi, A.; Hobbs, M.; Meyn, R. E. Clonogenic cell survival assay. *Methods Mol Med* 2005, 110, 21-28.
26. Deng, J.; Lee, K. W.; Sanchez, T.; Cui, M.; Neamati, N.; Briggs, J. M. Dynamic receptor based pharmacophore model development and its application in designing novel HIV-1 integrase inhibitors. *J Med Chem* 2005, 48, 1496-1505.
27. Carlson, H. A.; Masukawa, K. M.; Rubins, K.; Bushman, F. D.; Jorgensen, W. L.; Lins, R. D.; Briggs, J. M.; McCammon, J. A. Developing a dynamic pharmacophore model for HIV-1 integrase. *J Med Chem* 2000, 43, 2100-21 14.

TABLE 1

Selected Physiochemical Properties of the Tested Compounds[a]

| Comp. | Structure | M.W. | pKa | #HBA | #HBD | MLogP | PSA (Å$^2$) | Fitting value |
|---|---|---|---|---|---|---|---|---|
| 1 | 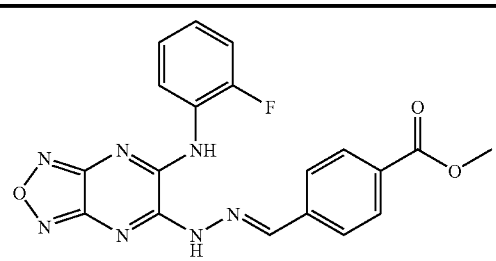 | 407.4 | | 10 | 2 | 2.8 | 133 | 4.1 |
| 2 | 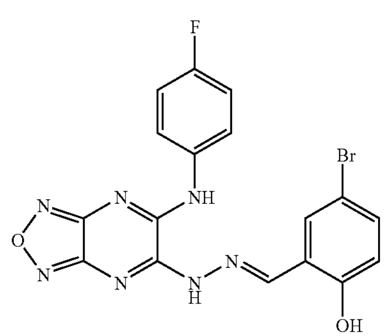 | 444.2 | 8.7 | 9 | 3 | 3.1 | 137 | 4.3 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 3 | 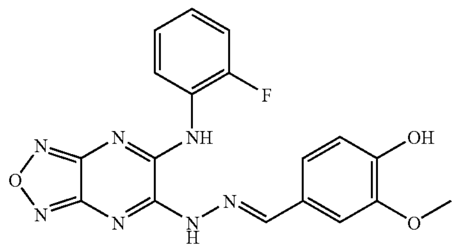 [SMILES: COc1cc(/C=N/Nc2nc3nonc3nc2Nc2ccccc2F)ccc1O] | 395.4 | 8.6 | 10 | 3 | 2.2 | 141 | 4.1 |
| 4 | 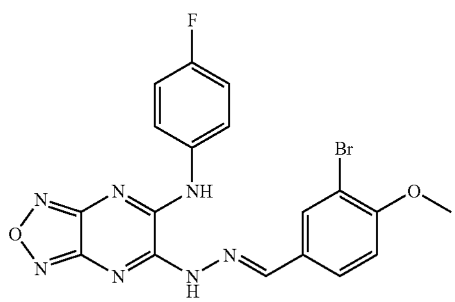 [SMILES: COc1ccc(/C=N/Nc2nc3nonc3nc2Nc2ccc(F)cc2)cc1Br] | 458.3 | | 9 | 2 | 3.3 | 107 | 4.5 |
| 5 | 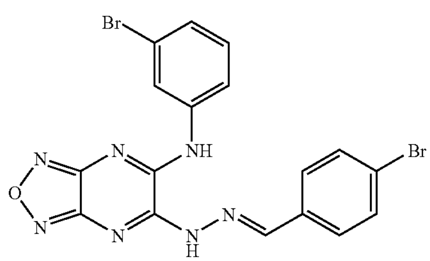 [SMILES: Brc1ccc(/C=N/Nc2nc3nonc3nc2Nc2cccc(Br)c2)cc1] | 489.1 | | 8 | 2 | 4.1 | 105 | 4.2 |
| 6 | 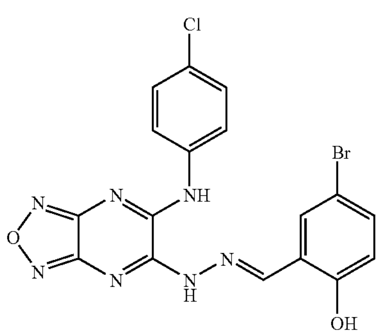 [SMILES: Oc1ccc(Br)cc1/C=N/Nc1nc2nonc2nc1Nc1ccc(Cl)cc1] | 460.7 | 8.8 | 9 | 3 | 3.2 | 137 | 4.3 |
| 7 | 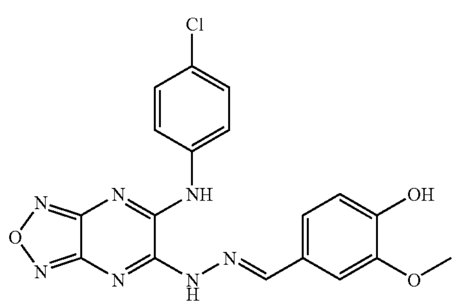 [SMILES: COc1cc(/C=N/Nc2nc3nonc3nc2Nc2ccc(Cl)cc2)ccc1O] | 411.8 | 8.7 | 10 | 3 | 2.4 | 143 | 4.6 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 8 | 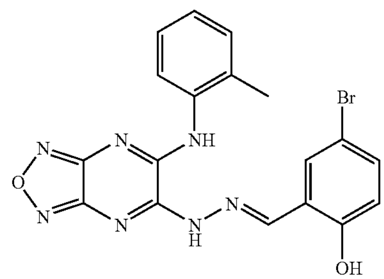 [SMILES: Cc1ccccc1Nc1nc2nonc2nc1N/N=C/c1cc(Br)ccc1O] | 440.3 | 8.9 | 9 | 3 | 32 | 132 | 4.2 |
| 9 | 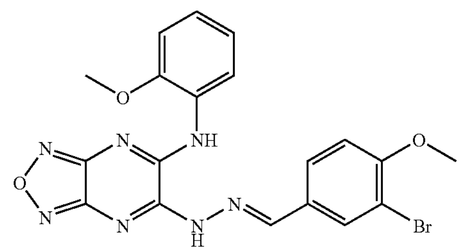 [SMILES: COc1ccc(/C=N/Nc2nc3nonc3nc2Nc2ccccc2OC)cc1Br] | 470.3 | | 10 | 2 | 2.7 | 106 | 5.0 |
| 10 | 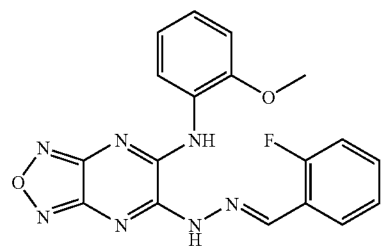 [SMILES: COc1ccccc1Nc1nc2nonc2nc1N/N=C/c1ccccc1F] | 379.3 | | 9 | 2 | 3.0 | 105 | 4.9 |
| 11 | 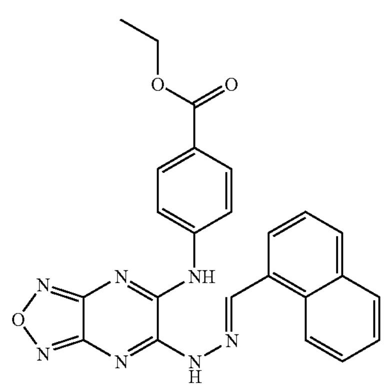 [SMILES: CCOC(=O)c1ccc(Nc2nc3nonc3nc2N/N=C/c2cccc3ccccc23)cc1] | 453.5 | | 10 | 2 | 3.7 | 136 | 4.5 |
| 12 | 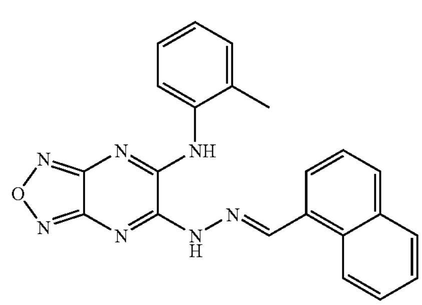 [SMILES: Cc1ccccc1Nc1nc2nonc2nc1N/N=C/c1cccc2ccccc12] | 395.4 | | 8 | 2 | 4.4 | 101 | 4.4 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 13 | 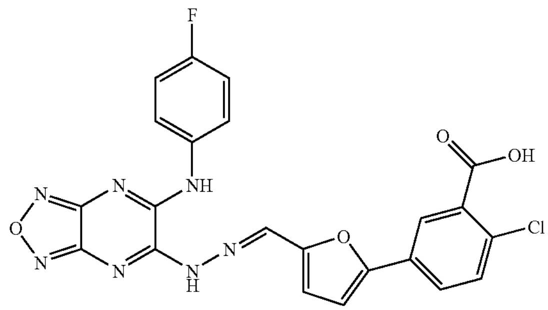 [SMILES: O=C(O)c1cc(-c2ccc(C=NNc3nc4nonc4nc3Nc3ccc(F)cc3)o2)ccc1Cl] | 493.8 | 5.5 | 11 | 3 | 2.8 | 186 | 4.3 |
| 14 | 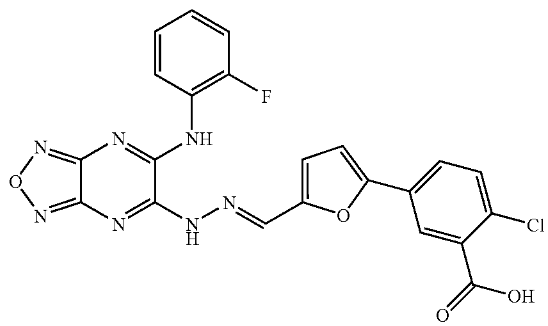 [SMILES: O=C(O)c1cc(-c2ccc(/C=N/Nc3nc4nonc4nc3Nc3ccccc3F)o2)ccc1Cl] | 493.8 | 5.5 | 11 | 3 | 2.8 | 184 | 4.2 |
| 15 | 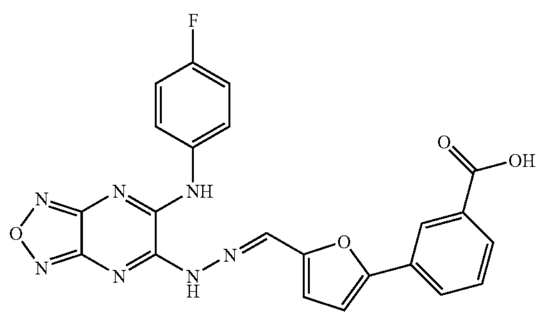 [SMILES: O=C(O)c1cccc(-c2ccc(C=NNc3nc4nonc4nc3Nc3ccc(F)cc3)o2)c1] | 459.4 | 5.7 | 11 | 3 | 2.6 | 194 | 4.3 |
| 16 | 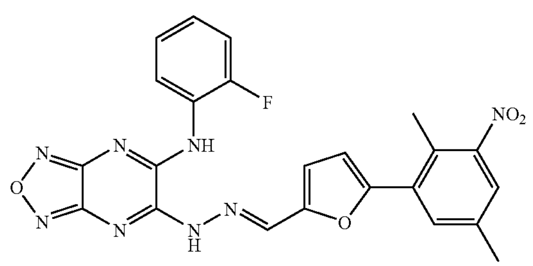 [SMILES: Cc1cc(-c2ccc(/C=N/Nc3nc4nonc4nc3Nc3ccccc3F)o2)c(C)c([N+](=O)[O-])c1] | 488.4 | | 11 | 2 | 3.9 | 170 | 4.1 |
| 17 | 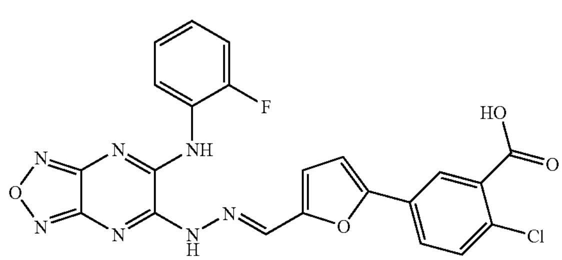 [SMILES: O=C(O)c1cc(-c2ccc(/C=N/Nc3nc4nonc4nc3Nc3ccccc3F)o2)ccc1Cl] | 493.8 | 5.5 | 11 | 3 | 2.8 | 184 | 4.2 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 18 | 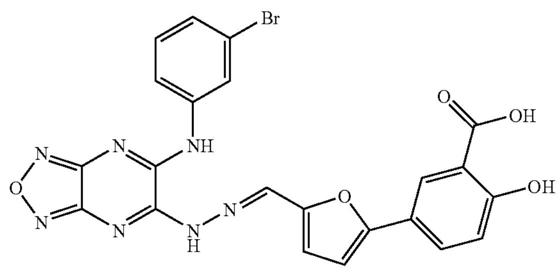 [SMILES: O=C(O)c1cc(-c2ccc(C=NNc3nc4nonc4nc3Nc3cccc(Br)c3)o2)ccc1O] | 536.3 | 6.2; 13.6 | 12 | 4 | 2.1 | 221 | 4.23 |
| 19 | 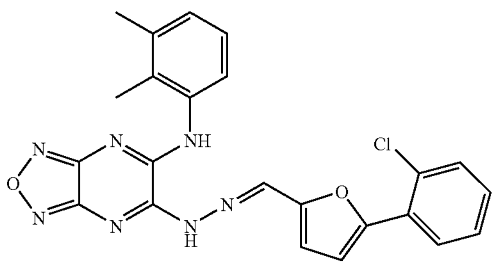 [SMILES: Cc1cccc(Nc2nc3nonc3nc2NN=Cc2ccc(-c3ccccc3Cl)o2)c1C] | 459.9 | | 9 | 2 | 4.0 | 97 | 4.6 |
| 20 | 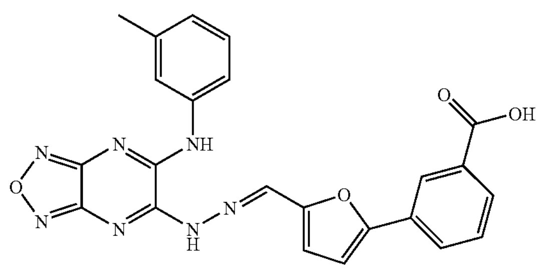 [SMILES: Cc1cccc(Nc2nc3nonc3nc2NN=Cc2ccc(-c3cccc(C(=O)O)c3)o2)c1] | 455.4 | 5.7 | 11 | 3 | 2.7 | 194 | 4.2 |
| 21 | 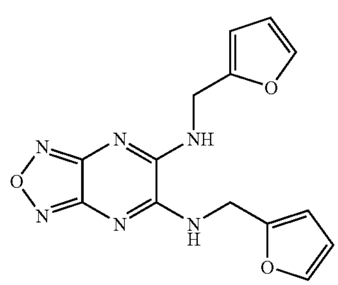 [SMILES: c1coc(CNc2nc3nonc3nc2NCc2ccco2)c1] | 312.3 | | 9 | 2 | 0.7 | 130 | 4.7 |
| 22 | 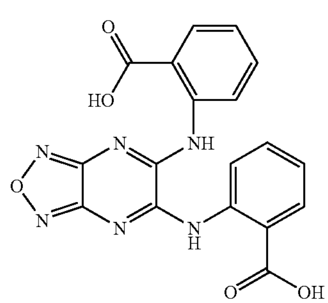 [SMILES: O=C(O)c1ccccc1Nc1nc2nonc2nc1Nc1ccccc1C(=O)O] | 392.3 | 6.0; 6.2 | 11 | 2 | −0.9 | 117 | 3.5 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 23 | 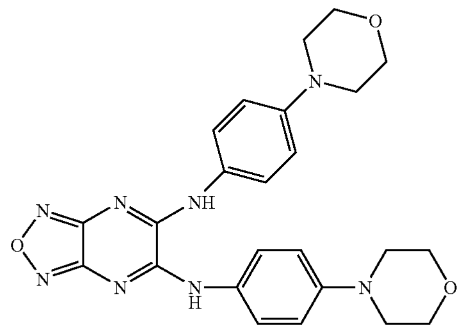 [SMILES: c1cc(N2CCOCC2)ccc1Nc1nc2nonc2nc1Nc1ccc(N2CCOCC2)cc1] | 474.5 | | 11 | 2 | 3.1 | 137 | 3.7 |
| 24 | 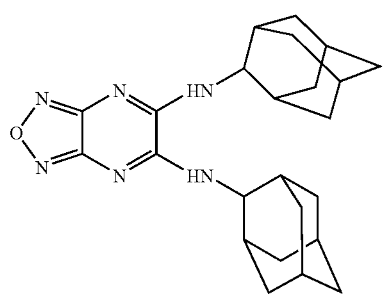 [SMILES: C1C2CC3CC1CC(C2)C3Nc1nc2nonc2nc1NC1C2CC3CC(C2)CC1C3] | 420.6 | | 7 | 2 | 4.9 | 101 | 4.1 |
| 25 | 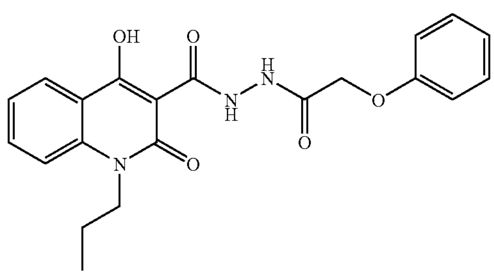 [SMILES: CCCn1c(=O)c(C(=O)NNC(=O)COc2ccccc2)c(O)c2ccccc21] | 395.4 | 4.7; 9.6; 10.3 | 7 | 3 | 2.3 | 129 | 4.3 |
| 26 | 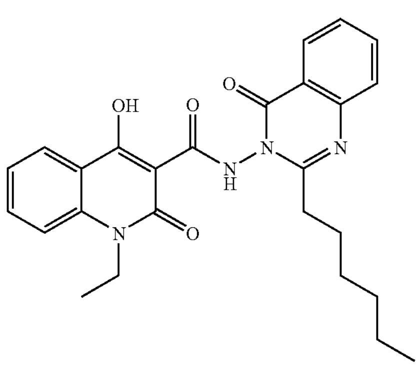 [SMILES: CCCCCCc1nc2ccccc2c(=O)n1NC(=O)c1c(O)c2ccccc2n(CC)c1=O] | 460.5 | 0.9; 3.4 | 6 | 2 | 3.6 | 79.3 | 4.5 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 27 | 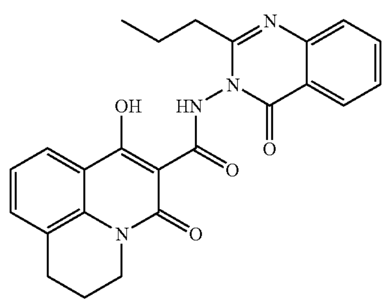 [SMILES: CCCc1nc2ccccc2c(=O)n1NC(=O)c1c(O)c2cccc3c2n(c1=O)CCC3] | 430.5 | 0.6 | 6 | 2 | 3.2 | 79 | 4.0 |
| 28 | 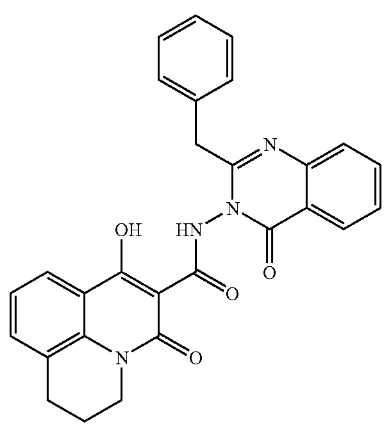 [SMILES: O=C(Nn1c(Cc2ccccc2)nc2ccccc2c1=O)c1c(O)c2cccc3c2n(c1=O)CCC3] | 478.5 | 0.6; 5.1 | 6 | 2 | 3.8 | 81 | 3.4 |
| 29 | 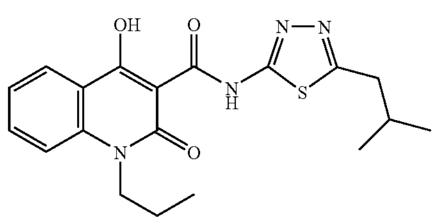 [SMILES: CCCn1c(=O)c(C(=O)Nc2nnc(CC(C)C)s2)c(O)c2ccccc21] | 386.5 | 2.1; 7.8 | 6 | 2 | 2.7 | 102 | 4.2 |
| 30 | 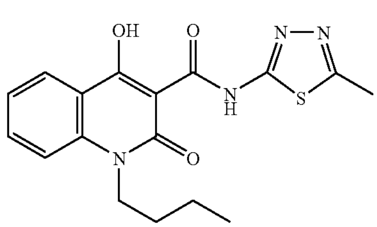 [SMILES: CCCCn1c(=O)c(C(=O)Nc2nnc(C)s2)c(O)c2ccccc21] | 358.4 | 2.0; 7.7 | 6 | 2 | 2.2 | 110 | 4.4 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 31 | 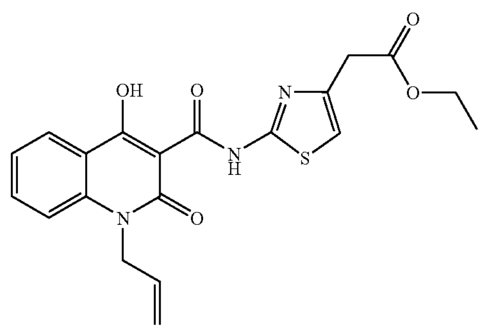 [SMILES: C=CCn1c(=O)c(C(=O)Nc2nc(CC(=O)OCC)cs2)c(O)c2ccccc21] | 413.4 | 2.6; 7.9 | 7 | 2 | 1.6 | 96 | 4.4 |
| 32 | 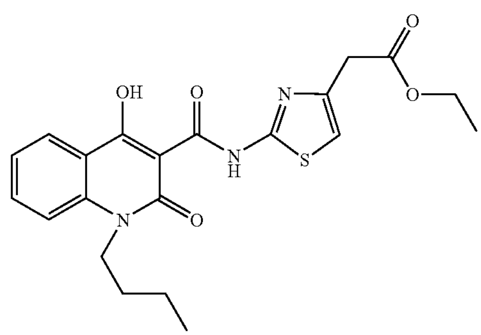 [SMILES: CCCCn1c(=O)c(C(=O)Nc2nc(CC(=O)OCC)cs2)c(O)c2ccccc21] | 429.5 | 2.8; 8.1 | 7 | 2 | 1.9 | 95 | 4.3 |
| 33 | 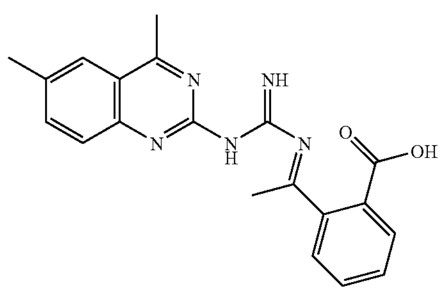 [SMILES: C/C(=N\C(=N)Nc1nc(C)c2cc(C)ccc2n1)c1ccccc1C(=O)O] | 361.4 | −0.8; 4.7 | 7 | 3 | 2.9 | 103 | 4.2 |
| 34 | 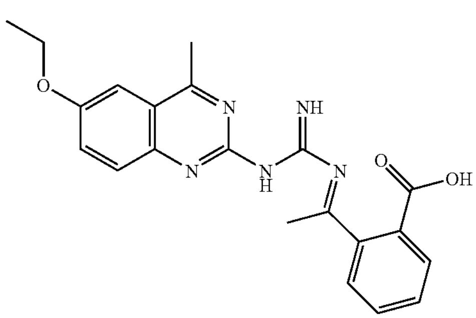 [SMILES: CCOc1ccc2nc(NC(=N)/N=C(\C)c3ccccc3C(=O)O)nc(C)c2c1] | 391.4 | −0.8; 4.7 | 8 | 3 | 2.6 | 104 | 4.4 |

TABLE 1-continued

Selected Physiochemical Properties of the Tested Compounds[a]

| Comp. | Structure | M.W. | pKa | # HBA | # HBD | MLogP | PSA (Å$^2$) | Fitting value |
|---|---|---|---|---|---|---|---|---|
| 35 | 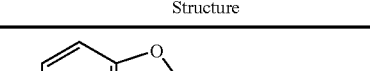 | 300.3 | −3.1 | 8 | 2 | 0.7 | 114 | 4.5 |

[a]All properties except fitting values were calculated by ADMET Predictor (SimulationsPlus, Inc.), and the fitting values of compound mapping against the phamacophore model were generated by Catalyst (Accelrys, Inc).
HBD: H-bond donor;
HBA: H-bond acceptor;
MlogP: Moriguchi octanol-water partition coefficient;
PSA: polar solvent accessible surface area A2.

TABLE 2

Cytotoxicity Data of Tested Compounds in a Panel of Cell Lines

| | IC$_{50}$, μM | | | | |
|---|---|---|---|---|---|
| Compound | HCT116 p53+/+ | HCT116 p53−/− | MDA-MB-435 | NIH3T3 | HEY |
| 1 | >10 | 10 | 5 | >10 | 10 |
| 2 | 1.5 ± 1 | 1.8 ± 0.7 | 7; 8 | 6 ± 1.4 | 1.3 ± 0.4 |
| 3 | >10 | >10 | >10 | >10 | 5 |
| 4 | 4 | 3; 2 | 10 | 6 | 10 |
| 5 | 2 | 1.1, 1.2 | >10 | 1 | 2; 3 |
| 6 | 2.7 ± 0.6 | 1.6 ± 0.7 | 4 ± 1 | 2 ± 0.5 | 1.6 ± 0.6 |
| 7 | >10 | 5.5 | >10 | >10 | 2 |
| 8 | 2 | 1.1 ± 0.4 | >10 | >10 | 5 |
| 9 | >20 | >10 | >20 | >10 | >10 |
| 10 | >10 | >10 | >10 | >10 | >10 |
| 11 | >10 | 2 | >10 | 2 | 4 |
| 12 | >10 | 10 | >10 | 10 | >10 |
| 13 | >10 | 7 | >10 | 10 | >10 |
| 14 | >10 | 7 | >10 | >10 | 10 |
| 15 | 5; 10 | 8, 7 | 3 | 10 | 6; 8 |
| 16 | 1.5 | 0.8 ± 0.1 | 4 | 2 | 0.8 |
| 17 | 7 ± 1 | >10 | >20 | >10 | 20, 15 |
| 18 | >10 | >10 | >10 | 11 | >10 |
| 19 | 3; 2 | 6; 4 | >10 | >10 | 3; 5 |
| 20 | >10 | >10 | >10 | 10 | 8 |
| 21 | >20 | >10 | >20 | >10 | >20 |
| 22 | >10 | >10 | >10 | >10 | >10 |
| 23 | >10 | >10 | >10 | >10 | >10 |
| 24 | 6; 8 | 9 ± 1 | 9 | 9 | 8 ± 1.7 |
| 25 | 10 | >10 | >20 | >10 | >10 |
| 26 | >20 | >10 | >20 | 20 | 20 |
| 27 | >20 | >10 | >20 | 12 | >20 |
| 28 | >20 | >10 | >10 | >10 | 19; 15 |
| 29 | >20 | >10 | >20 | >10 | >20 |
| 30 | 6 ± 3 | 8 | 7 | 5 | 10; 14 |
| 31 | 20 | >10 | >10 | >10 | >10 |
| 32 | 10 ± 1 | >10 | 20 | 8 | 15 |
| 33 | 18 | 5 | 17; 18 | 14 | 5; 3 |
| 34 | 20 | 10 | >20 | >10 | 7 |
| 35 | 5.0 | 4.2; 3.4 | 6 | 11, 6 | 3.5; 2 |

Values with standard deviation are from at least three independent experiments and others are as explicitly stated. Each experiment was generated from an average of four independent wells.

TABLE 3

Feature Mapping of the Top-ten Common Feature Hypotheses

| | | Model | | | | | | | | | |
|---|---|---|---|---|---|---|---|---|---|---|---|
| | | M1 | M2 | M3 | M4 | M5 | M6 | M7 | M8 | M9 | M10 |
| | | Features | | | | | | | | | |
| | | PHHAA | PHHAA | PHHAA | PHHAA | PHHAA | PHHAA | PHHAA | PHHAA | HHHAA | HHHAA |
| | Rank | 117.52 | 116.50 | 114.68 | 113.91 | 112.11 | 111.92 | 111.56 | 109.91 | 108.47 | 105.29 |
| Direct | R1 | 1 | 1 | 1 | 1 | 1 | 1 | 1 | 1 | 1 | 1 |
| Hit | R2 | 1 | 1 | 1 | 1 | 1 | 1 | 1 | 1 | 1 | 1 |
| Mask | R3 | 1 | 1 | 1 | 1 | 1 | 1 | 1 | 1 | 1 | 1 |
| | R4 | 1 | 1 | 1 | 1 | 1 | 1 | 1 | 1 | 1 | 1 |
| | R5 | 1 | 1 | 1 | 1 | 1 | 1 | 1 | 1 | 1 | 1 |
| | R6 | 1 | 1 | 1 | 1 | 1 | 1 | 1 | 1 | 1 | 1 |
| | R7 | 1 | 1 | 1 | 1 | 1 | 1 | 1 | 1 | 1 | 1 |
| | R8 | 1 | 1 | 1 | 1 | 1 | 1 | 1 | 1 | 1 | 1 |
| | R9 | 1 | 1 | 1 | 1 | 1 | 1 | 1 | 1 | 1 | 1 |
| | R10 | 1 | 1 | 1 | 1 | 1 | 1 | 1 | 1 | 1 | 1 |

TABLE 3-continued

Feature Mapping of the Top-ten Common Feature Hypotheses

| | | Model | | | | | | | | | |
|---|---|---|---|---|---|---|---|---|---|---|---|
| | | M1 | M2 | M3 | M4 | M5 | M6 | M7 | M8 | M9 | M10 |
| | | Features | | | | | | | | | |
| | Rank | PHHAA 117.52 | PHHAA 116.50 | PHHAA 114.68 | PHHAA 113.91 | PHHAA 112.11 | PHHAA 111.92 | PHHAA 111.56 | PHHAA 109.91 | HHHAA 108.47 | HHHAA 105.29 |
| Partial | R1 | 0 | 0 | 0 | 0 | 0 | 0 | 0 | 0 | 0 | 0 |
| Hit | R2 | 0 | 0 | 0 | 0 | 0 | 0 | 0 | 0 | 0 | 0 |
| Mask | R3 | 0 | 0 | 0 | 0 | 0 | 0 | 0 | 0 | 0 | 0 |
| | R4 | 0 | 0 | 0 | 0 | 0 | 0 | 0 | 0 | 0 | 0 |
| | R5 | 0 | 0 | 0 | 0 | 0 | 0 | 0 | 0 | 0 | 0 |
| | R6 | 0 | 0 | 0 | 0 | 0 | 0 | 0 | 0 | 0 | 0 |
| | R7 | 0 | 0 | 0 | 0 | 0 | 0 | 0 | 0 | 0 | 0 |
| | R8 | 0 | 0 | 0 | 0 | 0 | 0 | 0 | 0 | 0 | 0 |
| | R9 | 0 | 0 | 0 | 0 | 0 | 0 | 0 | 0 | 0 | 0 |
| | R10 | 0 | 0 | 0 | 0 | 0 | 0 | 0 | 0 | 0 | 0 |

TABLE 4

Cluster Analysis of the Common Feature Models MI-MI0 using the Hierarchical Average Linkage Method[a]

| | Number of clusters | | | | | | | |
|---|---|---|---|---|---|---|---|---|
| | 2 | 3 | 4 | 5 | 6 | 7 | 8 | 9 |
| M1 | $A_2$ | $A_3$ | $A_4$ | $A_5$ | $A_6$ | $A_7$ | $A_8$ | $A_9$ |
| M2 | $A_2$ | $A_3$ | $A_4$ | $A_5$ | $A_6$ | $A_7$ | $A_8$ | $A_9$ |
| M5 | $A_2$ | $A_3$ | $A_4$ | $B_5$ | $B_6$ | $B_7$ | $B_8$ | $B_9$ |
| M6 | $A_2$ | $A_3$ | $A_4$ | $B_5$ | $B_6$ | $C_7$ | $C_8$ | $C_9$ |
| M3 | $A_2$ | $B_3$ | $B_4$ | $C_5$ | $C_6$ | $D_7$ | $D_8$ | $D_9$ |
| M8 | $A_2$ | $B_3$ | $B_4$ | $C_5$ | $C_6$ | $D_7$ | $D_8$ | $E_9$ |
| M4 | $A_2$ | $B_3$ | $B_4$ | $C_5$ | $D_6$ | $E_7$ | $E_8$ | $F_9$ |
| M7 | $A_2$ | $B_3$ | $C_4$ | $D_5$ | $E_6$ | $F_7$ | $F_8$ | $G_9$ |
| M9 | $B_2$ | $C_3$ | $D_4$ | $E_5$ | $F_6$ | $G_7$ | $G_8$ | $H_9$ |
| M10 | $B_2$ | $C_3$ | $D_4$ | $E_5$ | $F_6$ | $G_7$ | $H_8$ | $I_9$ |

[a]The column indicates the total number of desired clusters, and the row indicates the total ten-model generated. The entries in the table indicate which cluster the certain model belongs to. The model with the same value as shown in table entry indicates belongs to the same cluster.

TABLE 5

Structures and Cytotoxicity of SMD6 and its Analogues on a Panel of Cancer Cell Lines

| | | | | $IC_{50}$, μM | | | |
|---|---|---|---|---|---|---|---|
| Comp. | Structure | M.W. | Hct116 p53−/− | Hct116 p53+/+ | SkBr-3 | HEY | MDA-MB-435 |
| 1-SMD6 | | 367.8 | 1.5 ± 0.1 | 1.0 ± 0.7 | 5.0 ± 1.0 | 3.5 ± 1.6 | 8.0 ± 0.5 |
| 2-SMD6-4 | | 379.8 | 2.1 ± 0.1 | 2.2 ± 0.8 | 7.4 ± 0.5 | 2.5 ± 0.4 | >10.0 |

TABLE 5-continued

Structures and Cytotoxicity of SMD6 and its Analogues on a Panel of Cancer Cell Lines

| Comp. | Structure | M.W. | IC$_{50}$, μM | | | | |
|---|---|---|---|---|---|---|---|
| | | | Hct116 p53−/− | Hct116 p53+/+ | SkBr-3 | HEY | MDA-MB-435 |
| 3-SMD6-5 | | 299.4 | 8.1 ± 0.6 | >10.0 | >10.0 | >10.0 | >10.0 |
| 4-SMD6-8 | | 343.7 | 2.1 ± 0.5 | 1.6 ± 0.4 | 2.5 ± 0.5 | 2.2 ± 0.3 | 2.2; 0.3 |

TABLE 6

Structures and Cytotoxicity of SMD18 and its Analogues on a Panel of Cancer Cell Lines

| Comp. | Structure | M.W. | IC$_{50}$, μM | | | | |
|---|---|---|---|---|---|---|---|
| | | | Hct116 p53−/− | Hct116 p53+/+ | SkBr-3 | HEY | MDA-MB-435 |
| 5-SMD18 | | 302.3 | 6.5 ± 0 | 7.2 ± 0.1 | 2.5 ± 0.8 | 7.2 ± 0.2 | 7 ± 1.1 |
| 6-SMD18-1 | | | 4 ± 2 | 3.4 ± 0.2 | >10 | | 9.5 |

TABLE 6-continued

Structures and Cytotoxicity of SMD18 and its Analogues on a Panel of Cancer Cell Lines

| Comp. | Structure | M.W. | IC$_{50}$, μM | | | | |
|---|---|---|---|---|---|---|---|
| | | | Hct116 p53−/− | Hct116 p53+/+ | SkBr-3 | HEY | MDA-MB-435 |
| 7-SMD18-8 | 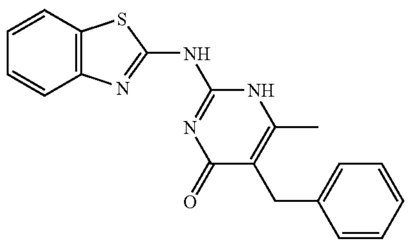 [SMILES: Cc1[nH]c(Nc2nc3ccccc3s2)nc(=O)c1Cc1ccccc1] | | >10; 7.2 | 10; >10 | >10 | | >10 |
| 8-SMD18-14 | 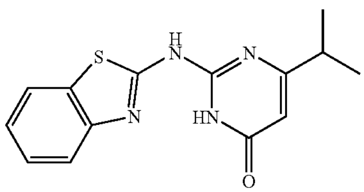 [SMILES: CC(C)c1cc(=O)[nH]c(Nc2nc3ccccc3s2)n1] | | 3.6 ± 1.8 | 4.5 ± 1.5 | >10 | | >10 |
| 9-SMD18-15-BAS 12534660 | 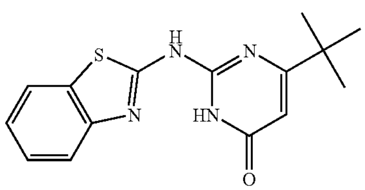 [SMILES: CC(C)(C)c1cc(=O)[nH]c(Nc2nc3ccccc3s2)n1] | | 9.9 | 9.9 | >10 | | 7.5 |

TABLE 7

Structures and Cytotoxicity of SMD58 and its Analogues on a Panel of Cancer Cell Lines

| Comp. | Structure | M.W. | IC$_{50}$, μM | | | | |
|---|---|---|---|---|---|---|---|
| | | | Hct116 p53−/− | Hct116 p53+/+ | SkBr-3 | HEY | MDA-MB-435 |
| 10-SMD58 | 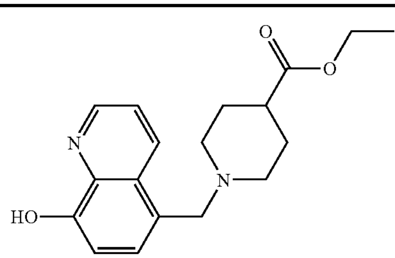 | 314.3 | 0.3 | <1.0; 0.3 | 3.5 ± 0.5 | 0.5 | 2.4 ± 1.5 |
| 11-SMD58-1 | 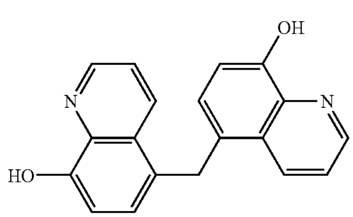 [SMILES: Oc1ccc(Cc2ccc(O)c3ncccc23)c2cccnc12] | 302.3 | 0.25 ± 0.5 | 0.45 | 1.4 ± 0.8 | 0.1 | 2.8 ± 1.7 |

TABLE 7-continued
Structures and Cytotoxicity of SMD58 and its Analogues on a Panel of Cancer Cell Lines
| Comp. | Structure | M.W. | Hct116 p53−/− | Hct116 p53+/+ | SkBr-3 | HEY | MDA-MB-435 |
|---|---|---|---|---|---|---|---|
| 12-SMD58 | 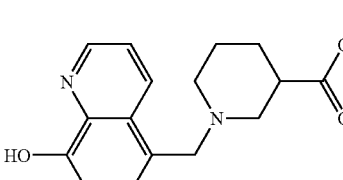 | 314.4 | 2 ± 0.1 | 1.6 ± 0.4 | 2.2 ± 0.9 | 0.9 | 4.2 ± 1.2 |
| 13-SMD58-5 | 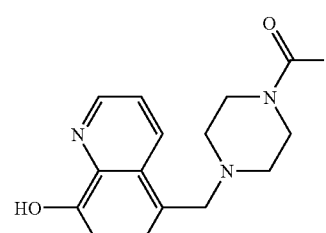 | 315.4 | 1 ± 0.1 | 2.1 ± 0.2 | 3.7 ± 0.5 | 1.9 | 5.3 ± 0.1 |
| 14-SMD58-7 | 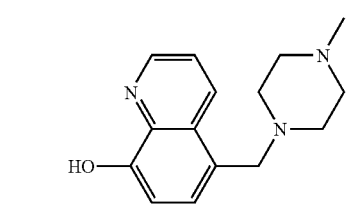 [SMILES: CN1CCN(Cc2ccc(O)c3ncccc23)CC1] | 254.3 | 1.7 ± 0.2 | 0.7 ± 0.4 | 3.2 ± 0.1 | 0.4 | 3.9 ± 0.1 |
| 15-SMD58-8 | 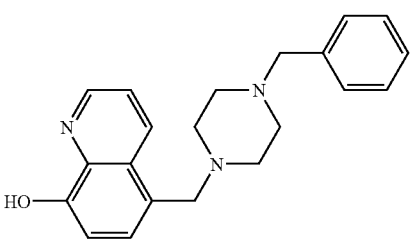 [SMILES: Oc1ccc(CN2CCN(Cc3ccccc3)CC2)c2cccnc12] | 333.4 | 2.5 ± 1.6 | 1.7 ± 0.7 | 1.7 ± 0.7 | 1.8 ± 0.7 | 5.4 ± 0.7 |
| 16-SMD58-11 | 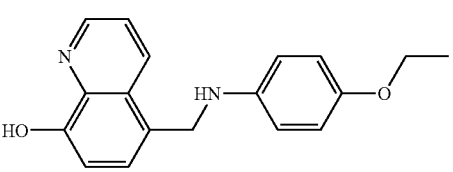 [SMILES: CCOc1ccc(NCc2ccc(O)c3ncccc23)cc1] | 294.4 | 1.2 ± 0.2 | 2.3 ± 0.1 | 3 ± 1.3 | 1.7 ± 0.1 | 4.9 ± 1.1 |
| 17-SMD58-12 | 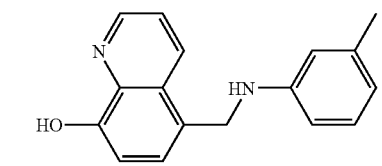 | 264.3 | 1.9 ± 0.4 | 1.8 ± 0.4 | 4 ± 0.5 | 1.5 ± 0.8 | 6.6 |
| 18-SMD58-13 | 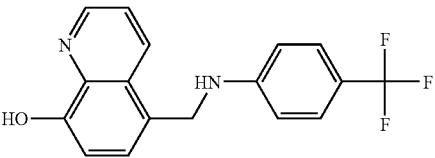 [SMILES: Oc1ccc(CNc2ccc(C(F)(F)F)cc2)c2cccnc12] | 318.3 | 2 ± 0.1 | 1.6 ± 0.1 | 2.8 ± 0.5 | 1.2 ± 0.1 | 5.2 ± 0.4 |

TABLE 7-continued

Structures and Cytotoxicity of SMD58 and its Analogues on a Panel of Cancer Cell Lines

| Comp. | Structure | M.W. | IC$_{50}$, μM | | | | |
| --- | --- | --- | --- | --- | --- | --- | --- |
| | | | Hct116 p53−/− | Hct116 p53+/+ | SkBr-3 | HEY | MDA-MB-435 |
| 19-SMD58-14 | 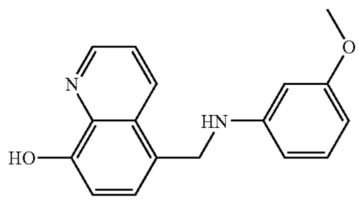 [SMILES: COc1cccc(NCc2ccc(O)c3ncccc23)c1] | 280.3 | 2.1 ± 0.1 | 1.3 ± 0.9 | 2.9 ± 0.3 | 1.9 | 5 ± 0.9 |
| 20-SMD58-18 | 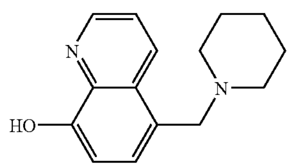 [SMILES: Oc1ccc(CN2CCCCC2)c2cccnc12] | 242.3 | 6.5 ± 0.8 | 6.8 ± 1.3 | 8.6 ± 1.4 | 5 ± 1.6 | 8.9 |
| 21-SMD58-19 | 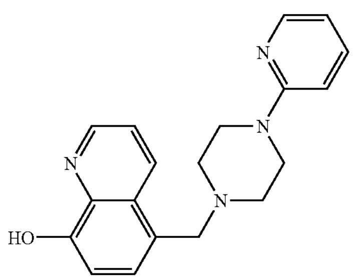 [SMILES: Oc1ccc(CN2CCN(c3ccccn3)CC2)c2cccnc12] | 320.4 | 2.2 ± 0.1 | 2.6 ± 0.7 | 3 ± 1 | 2.8 ± 0.6 | 2.7 |
| 22-SMD58-20 | 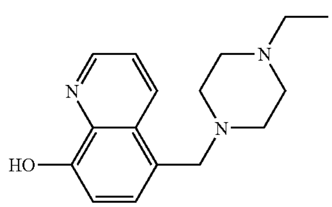 [SMILES: CCN1CCN(Cc2ccc(O)c3ncccc23)CC1] | 271.4 | 2.1 ± 1.2 | 2.1 ± 0 | 4.1 ± 0.1 | 1.4 ± 0.2 | 7.2 ± 0.4 |
| 23-SMD58-22 | 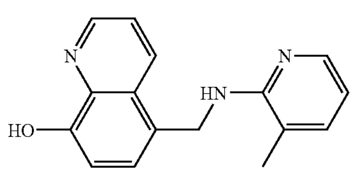 | 265.3 | 1.5 ± 0.1 | 1.4 ± 0.4 | 3.3 ± 0.7 | 2.8 | 3.1 ± 0.6 |
| 24-SMD58-23 | 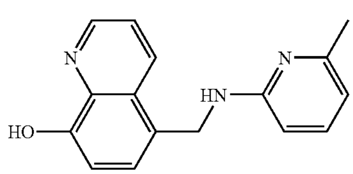 [SMILES: Cc1cccc(NCc2ccc(O)c3ncccc23)n1] | 265.3 | 1.6 ± 0.3 | 2.8 ± 0.1 | 3.6 ± 0.5 | 2.3 ± 0.3 | 2.3 |

TABLE 7-continued
Structures and Cytotoxicity of SMD58 and its Analogues on a Panel of Cancer Cell Lines
| Comp. | Structure | M.W. | Hct116 p53−/− | Hct116 p53+/+ | SkBr-3 | HEY | MDA-MB-435 |
|---|---|---|---|---|---|---|---|
| 25-SMD58-26 | 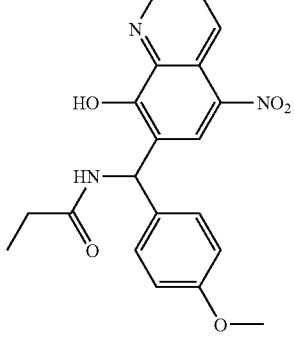 | 381.4 | 7.1 ± 1.1 | 6.8 ± 0.2 | >10; >10 | 3.2 ± 0 | 7.5 |
| 26-SMD58-27 | 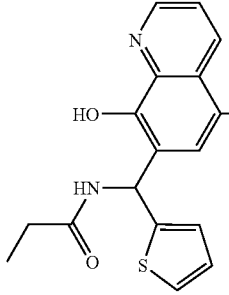 | 357.4 | 4.2 ± 1.2 | 5.0 ± 0.4 | 4.6 ± 0.8 | 3.2 ± 0.8 | 5.6 |
What is claimed is:
1. An anticancer compound selected from the group consisting of
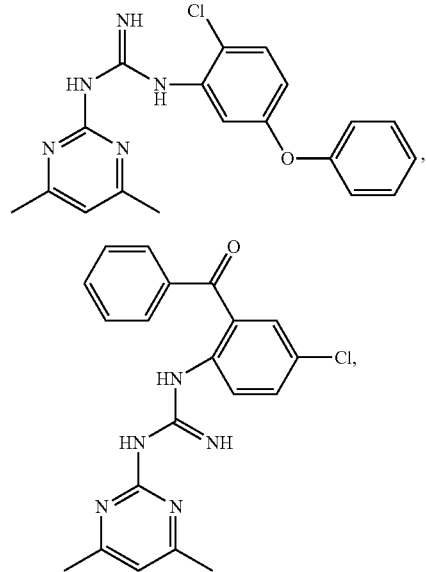
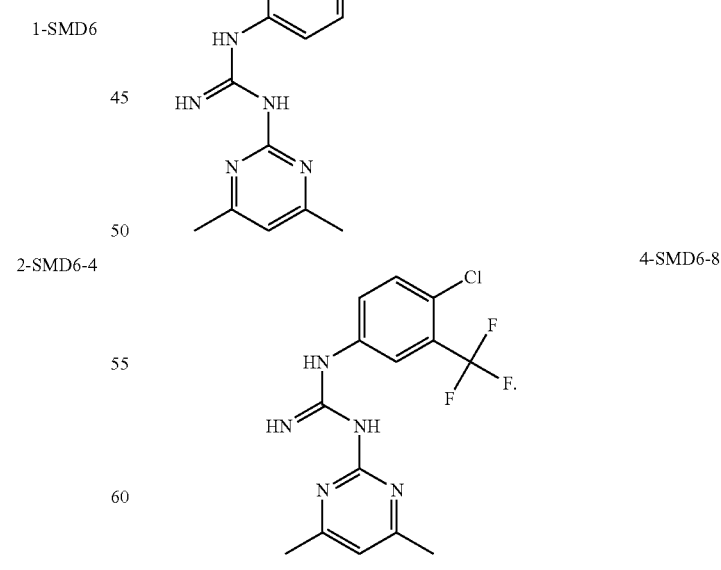
* * * * *